(12) United States Patent
Braganca et al.

(10) Patent No.: US 11,112,468 B2
(45) Date of Patent: Sep. 7, 2021

(54) MAGNETORESISTIVE SENSOR ARRAY FOR MOLECULE DETECTION AND RELATED DETECTION SCHEMES

(71) Applicant: Western Digital Technologies, Inc., San Jose, CA (US)

(72) Inventors: Patrick Braganca, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 129 days.

(21) Appl. No.: 16/659,383

(22) Filed: Oct. 21, 2019

(65) Prior Publication Data

US 2020/0326391 A1    Oct. 15, 2020

Related U.S. Application Data

(60) Provisional application No. 62/833,237, filed on Apr. 12, 2019.

(51) Int. Cl.
*G01R 33/09* (2006.01)
*G11B 5/39* (2006.01)
(Continued)

(52) U.S. Cl.
CPC ......... *G01R 33/093* (2013.01); *C12Q 1/6869* (2013.01); *C12Q 1/6874* (2013.01);
(Continued)

(58) Field of Classification Search
None
See application file for complete search history.

(56) References Cited

U.S. PATENT DOCUMENTS

| 5,302,509 A | 4/1994 | Cheeseman |
| 6,037,167 A | 3/2000 | Adelman et al. |

(Continued)

FOREIGN PATENT DOCUMENTS

| EP | 1544310 A2 | 6/2005 |
| EP | 3208627 A1 | 8/2017 |

(Continued)

OTHER PUBLICATIONS

A. Seki, et al., "Study of the heating characteristics and mechanisms of magnetic nanoparticles over a wide range of frequencies and amplitudes of an alternating magnetic field," Journal of Physics: Conference Series 521 (2014).

(Continued)

*Primary Examiner* — Jefferson A Evans
(74) *Attorney, Agent, or Firm* — Jacobsen IP Law; Krista S. Jacobsen

(57) ABSTRACT

A sensing device comprises a plurality of magnetoresistive (MR) sensors, at least one fluidic channel, and detection circuitry coupled to the MR sensors. Each MR sensor is configured to detect the presence of molecules (e.g., biologic molecules) labeled by magnetic nanoparticles (MNPs). The sensors are encapsulated by an insulating material that protects the sensors from the contents of the at least one fluidic channel. The insulating material has a surface within the fluidic channel that provides sites for binding the molecules to be detected. The detection circuitry is configured to detect (a) a characteristic of magnetic noise of each MR sensor, the characteristic being influenced by a presence or absence of one or more MNPs at each site, or (b) a change in resistance, current, and/or voltage drop of each MR sensor, wherein the change is influenced by the presence or absence of one or more MNPs at each site.

36 Claims, 15 Drawing Sheets

(51) Int. Cl.
  *G11B 5/02* (2006.01)
  *C12Q 1/6874* (2018.01)
  *G01R 33/12* (2006.01)
  *C12Q 1/6869* (2018.01)
(52) U.S. Cl.
  CPC ..... *G01R 33/1276* (2013.01); *G01R 33/1284* (2013.01); *G11B 5/02* (2013.01); *G11B 5/3903* (2013.01); *G11B 5/3945* (2013.01); *C12Q 2563/107* (2013.01); *G11B 5/3909* (2013.01)

(56) References Cited

U.S. PATENT DOCUMENTS

| | | |
|---|---|---|
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |
| 8,432,644 B2 | 4/2013 | Braganca et al. |
| 8,462,461 B2 | 6/2013 | Braganca et al. |
| 8,513,029 B2 | 8/2013 | Zhou |
| 8,553,346 B2 | 10/2013 | Braganca et al. |
| 8,570,677 B2 | 10/2013 | Braganca et al. |
| 8,597,881 B2 | 12/2013 | Milton et al. |
| 8,652,810 B2 | 2/2014 | Adessi et al. |
| 8,654,465 B2 | 2/2014 | Braganca et al. |
| 8,675,309 B2 | 3/2014 | Braganca et al. |
| 8,728,729 B2 | 5/2014 | Bridgham et al. |
| 8,728,825 B2 | 5/2014 | Wang et al. |
| 9,121,062 B2 | 9/2015 | Balasubramanian et al. |
| 9,273,354 B2 | 3/2016 | Bridgham et al. |
| 9,297,006 B2 | 3/2016 | Adessi et al. |
| 9,453,258 B2 | 9/2016 | Kain et al. |
| 9,464,107 B2 | 10/2016 | Wegener et al. |
| 9,587,275 B2 | 3/2017 | Emig et al. |
| 9,605,310 B2 | 3/2017 | Balasubramanian et al. |
| 9,640,748 B2 | 5/2017 | Gotsmann et al. |
| 9,823,316 B2 * | 11/2017 | Wang ................ G01N 35/0098 |
| 10,203,379 B2 | 2/2019 | Wang et al. |
| 10,591,440 B2 | 3/2020 | Astier et al. |
| 2002/0119470 A1 * | 8/2002 | Nerenberg ............ G01N 27/745 435/6.11 |
| 2004/0219695 A1 * | 11/2004 | Fox .................... G01N 27/745 436/526 |
| 2005/0054081 A1 | 3/2005 | Hassard et al. |
| 2007/0114180 A1 * | 5/2007 | Ramanathan .......... B82Y 25/00 210/695 |
| 2007/0264159 A1 * | 11/2007 | Graham ............ G01N 33/54373 422/400 |
| 2008/0218165 A1 * | 9/2008 | Kahlman ......... G01N 33/54326 324/260 |
| 2008/0241569 A1 | 10/2008 | Qin et al. |
| 2009/0139908 A1 * | 6/2009 | Zhou ....................... B03C 1/033 209/225 |
| 2009/0148857 A1 | 6/2009 | Srivastava et al. |
| 2009/0206832 A1 * | 8/2009 | Kahlman ............ G01R 33/1269 324/252 |
| 2009/0208957 A1 | 8/2009 | Korlach et al. |
| 2010/0039105 A1 | 2/2010 | Ryan et al. |
| 2010/0111768 A1 | 5/2010 | Banerjee et al. |
| 2010/0207631 A1 | 8/2010 | McDowell |
| 2010/0231214 A1 | 9/2010 | Zhou |
| 2010/0232075 A1 * | 9/2010 | Zhou .................... G01N 24/088 360/324.12 |
| 2011/0315635 A1 * | 12/2011 | Hayden .................... G01N 1/40 210/695 |
| 2012/0295262 A1 | 11/2012 | Ronaghi et al. |
| 2013/0285648 A1 * | 10/2013 | Kim ..................... G01N 27/745 324/201 |
| 2014/0008281 A1 | 1/2014 | Ramanathan et al. |
| 2014/0139214 A1 | 5/2014 | Park et al. |
| 2017/0304825 A1 * | 10/2017 | Issadore ............. B01L 3/502776 |
| 2018/0074016 A1 * | 3/2018 | Chen ................... G01N 27/745 |
| 2018/0237850 A1 * | 8/2018 | Mandell ............... G01R 33/093 |
| 2019/0283025 A1 * | 9/2019 | Brenk ............... B01L 3/502738 |
| 2019/0317167 A1 * | 10/2019 | Laborde .............. G01N 33/558 |
| 2019/0390267 A1 | 12/2019 | Astier et al. |
| 2020/0284856 A1 * | 9/2020 | Zhang .................... G01N 27/76 |
| 2021/0047681 A1 | 2/2021 | Mendonsa et al. |
| 2021/0047682 A1 | 2/2021 | Mendonsa et al. |

FOREIGN PATENT DOCUMENTS

| | | |
|---|---|---|
| WO | 2005047864 A3 | 9/2005 |
| WO | 2016183218 A1 | 11/2016 |
| WO | 2017030999 A1 | 2/2017 |
| WO | 2018017884 A1 | 1/2018 |
| WO | 2019068204 A1 | 4/2019 |

OTHER PUBLICATIONS

A.M. Sydor et al., "Super-Resolution Microscopy: From Single Molecules to Supramolecular Assemblies," Trends in Cell Biology, Dec. 2015, vol. 25, No. 12, pp. 730-748.

C.H. Smith et al., "High-resolution giant magnetoresistance on-chip arrays for magnetic imaging," Journal of Applied Physics 93, 6864 (2003).

D. Ross et al., "Temperature Measurement in Microfluidic Systems Using a Temperature-Dependent Fluorescent Dye," Anal. Chem. 2001, 73, 17, 4117-4123, Jul. 24, 2001.

2PHOTOzine.com, "Complete Guide to Image Sensor Pixel Size," Aug. 2, 2016, available at https://www.ephotozine.com/article/complete-guide-to-image-sensor-pixel-size-29652.

F. Grasset et al., "Synthesis, magnetic properties, surface modification and cytotoxicity evaluation of Y3Fe5-xAlxO12 (0?x?2) garnet submicron particles for biomedical applications," Journal of Magnetism and Magnetic Materials, vol. 234, Issue 3, Sep. 2001, pp. 409-418.

F. Menges et al., "Temperature mapping of operating nanoscale devices by scanning probe thermometry," Nature Communications, 7:10874, Mar. 3, 2016.

Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).

Illumina, "NovaSeq 6000 Sequencing System," 2019, available at https://www.illumina.com/systems/sequencing-platforms/novaseq.html.

International Search Report from PCT App. No. PCT/US2016/046888, dated Oct. 26, 2016.

J. Sakakibara et al., "Measurements of thermally stratified pipe flow using image-processing techniques," Experiments in Fluids, Dec. 1993, vol. 16, Issue 2, pp. 82-96.

(56) References Cited

OTHER PUBLICATIONS

John Pearce, et al., "Magnetic Heating of Nanoparticles: The Importance of Particle Clustering to Achieve Therapeutic Temperatures," Journal of Nanotechnology in Engineering and Medicine, Feb. 2014, vol. 4 / 011007-1.

Lin Gui and Carolyn L. Ren, "Temperature measurement in microfluidic chips using photobleaching of a fluorescent thin film," Applied Physics Letters 92, 024102, 2008.

M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.

N. X. Phuc, et al., "Tuning of the Curie Temperature in La1-xSrxMn1-yTiyO3" J. Korean Phy. Soc., vol. 52, No. 5, May 2008, pp. 1492-1495.

N.R. Patil et al., "Effect of temperature on the fluorescence emission of ENCTTTC in different nonpolar solvents," Can. J. Phys. 91: 971-975 (2013).

R. Giri, "Temperature effect study upon the fluorescence emission of substituted coumarins," Spectrochimica Acta Part A: Molecular Spectroscopy, vol. 48, Issue 6, Jun. 1992, p. 843-848.

S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.

S.I. Kiselev et al., "Microwave oscillations of a nanomagnet driven by a spin-polarized current," Nature 425, pp. 380-383, 2003.

W. Andrä, "Temperature distribution as function of time around a small spherical heat source of local magnetic hyperthermia," Journal of Magnetism and Magnetic Materials, vol. 194, Issues 1-3, Apr. 1999, pp. 197-203.

Weifeng Shen et al., "Detection of DNA labeled with magnetic nanoparticles using MgO-based magnetic tunnel function sensors," Journal of Applied Physics 103, 07A306 (2008).

E. du Trémolet de Lacheisserie, D. Gignoux, and M. Schlenker (editors), Magnetism: Materials and Applications, vol. 2. Springer, 2005.

E. Hall, "On a New Action of the Magnet on Electric Currents," American Journal of Mathematics, vol. 2, 287, 1879.

G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.

International Search Report and Written Opinion from PCT Application No. PCT/US2020/027290 (filed Apr. 8, 2020), dated Jun. 25, 2020.

International Search Report and Written Opinion from PCT Application No. PCT/US2019/068131 (filed Dec. 20, 2019), dated Apr. 1, 2020.

International Search Report and Written Opinion from PCT Application No. PCT/US2019/068535 (filed Dec. 26, 2019), dated Apr. 26, 2020.

International Search Report and Written Opinion from PCT Application No. PCT/US2020/014707 (filed Jan. 23, 2020), dated May 11, 2020.

International Search Report and Written Opinion from PCT Application No. PCT/US2020/021776 (filed Mar. 9, 2020), dated Sep. 1, 2020.

International Search Report and Written Opinion from PCT Application No. PCT/US2020/023069 (filed Mar. 17, 2020), dated Jul. 20, 2020.

International Search Report and Written Opinion from PCT Application No. PCT/US2020/023078 (filed Mar. 17, 2020), dated Jul. 19, 2020.

International Search Report and Written Opinion from PCT Application No. PCT/US2020/035915 (filed Jun. 3, 2020), dated Aug. 26, 2020.

J. C. Slonczewski, "Current-driven excitation of magnetic multilayers," Journal of Magnetism and Magnetic Materials, vol. 159, L1, 1996.

L. Berger, "Emission of spin waves by a magnetic multilayer traversed by a current," Physical Review B, vol. 54, 9353, 1996.

Lany, M., G. Boero, and R. S. Popovic. "Superparamagnetic microbead inductive detector". Review of scientific instruments 76.8 (2005): 084301.

Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.

M. Díaz-Michelena, "Small Magnetic Sensors for Space Applications," Sensors, vol. 9, 2271, 2009.

Michael L. Metzker, "Sequencing Technologies—the Next Generation," Nature Rev. Genet. 11: 31-46 (2009).

Miller, M. M., et al. "A DNA array sensor utilizing magnetic microbeads and magnetoelectronic detection". Journal of Magnetism and Magnetic Materials 225.1-2 (2001): 138-144.

P. Anderson, J. Rowell, "Probable Observation of the Josephson Superconducting Tunneling Effect," Physical Review Letters, vol. 10, 230, 1963.

P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.

P. Namdari, H. Daraee, and A. Eatemadi, "Recent Advances in Silicon Nanowire Biosensors: Synthesis Methods, Properties and Applications", Nanoscale Research Letters, vol. 11, 406, 2016.

Quynh, L. K., et al. Detection of magnetic nanoparticles using simple AMR sensors in Wheatstone bridge. Journal of Science: Advanced Materials and Devices, 2016, 1.1: 98-102.

R. C. Jaklevic, J. Lambe, A. H. Silver & J. E. Mercereau, "Quantum Interference Effects in Josephson Tunneling," Physical Review Letters, vol. 12, 159, 1964.

R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions on Magnetics, vol. 48, 1758, 2012.

Rabehi, A., Electromagnetic microsystem for the detection of magnetic nanoparticles in a microfluidic structure for immunoassays (Doctoral dissertation). Jan. 29, 2020.

Rauwerdink, A. M., Giustini, A. J., & Weaver, J. B. (2010). Simultaneous quantification of multiple magnetic nanoparticles. Nanotechnology, 21(45), 455101.

Riedinger, A., Guardia, P., Curcio, A., Garcia, M. A., Cingolani, R., Manna, L., & Pellegrino, T. (2013). Subnanometer local temperature probing and remotely collrolled drug release based on azo-functionalized iron oxide nanoparticles. Nano letters, 13(6), 2399-2406.

Srimani T. et al., "High Sensitivity Biosensor using Injection Locked Spin Torque Nano-Oscillators," arXiv:1511.09072, Nov. 2015.

Tang, C., He, Z., Liu, H., Xu, Y., Huang, H., Yang, G., . . . & Chen, Z. (2020). Application of magnetic nanoparticles in nucleic acid detection. Journal of Nanobiotechnology, 18, 1-19. Apr. 21, 2020.

Wang, W., & Jiang, Z., "Thermally assisted magnetic tunneling junction for biosensing applications," IEEE Transactions on Magnetics, 43(6), 2406-2408, Jun. 30, 2007.

Weijun Zhou, et al., "Novel dual fluorescence temperature-sensitive chameleon DNA-templated nanocluster pair for intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).

Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.

Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.

Ye, F., Zhao, Y., El-Sayed, R., Muhammed, M., & Hassan, M. (2018). Advances in nanotechnology for cancer biomarkers. Nano Today, 18, 103-123.

Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.

(56) References Cited

OTHER PUBLICATIONS

International Search Report from international application No. PCT/US2019/068131 (filed Dec. 20, 2019), dated Apr. 1, 2020.
L.K. Quynh et al., "Detection of magnetic nanoparticles using simple AMR sensors in Wheatstone bridge," Journal of Science: Advanced Materials and Devices 1 (2016) pp. 98-102.
Written Opinion of the International Searching Authority from international application No. PCT/US2019/068131 (filed Dec. 20, 2019), dated Apr. 1, 2020.
U.S. Appl. No. 62/833,130, filed Apr. 12, 2019, Yann Astier.
B. N. Engel, et al., "A 4-Mb Toggle MRAM Based on a Novel Bit and Switching Method," IEEE Transactions on Magnetics, vol. 41, No. 1, Jan. 2005.
C. Chappert et al., "The emergence of spin electronics in data storage," Nature Materials, Dec. 2007.
M. Aslam et al., "Silica encapsulation and magnetic properties of FePt nanoparticles," Journal of Colloid and Interface Science 290 (2005) 444-449.
M.T. Tlili et al., "Magnetic, Electrical Properties and Spin-Glass Effect of Substitution of Ca for Pr in $Ca_{2-x}Pr_xMnO_4$ Compounds," The Open Surface Science Journal, 2009, vol. 1, pp. 54-58.
T. Nagasawa et al., "Delay detection of frequency modulation signal from a spin-torque oscillator under a nanosecond-pulsed magnetic field," Journal of Applied Physics, vol. 111, 07C908 (2012).

\* cited by examiner

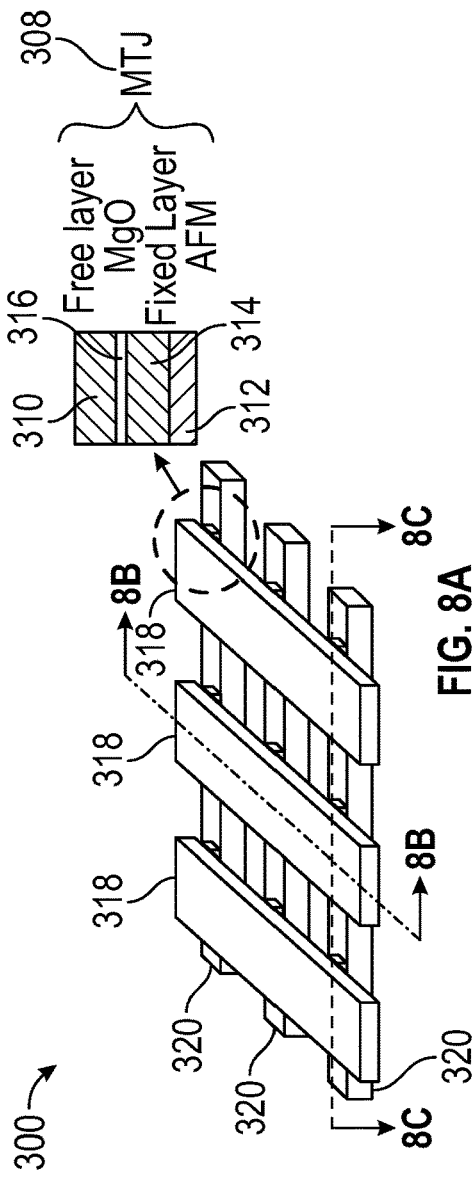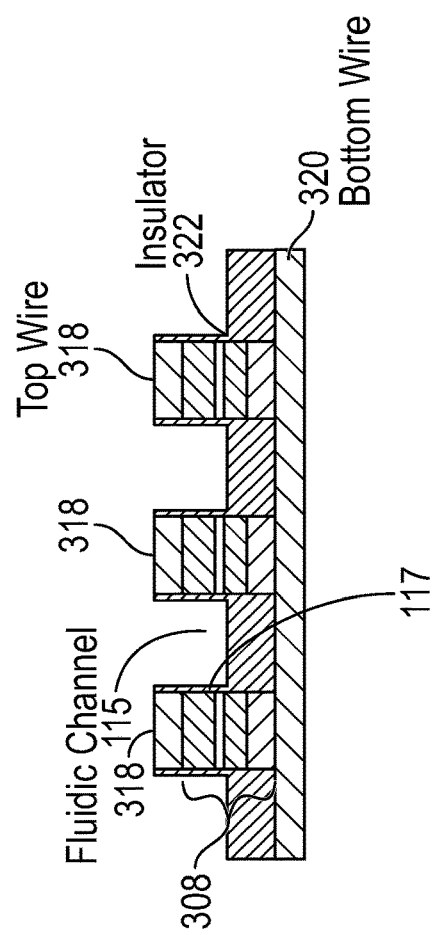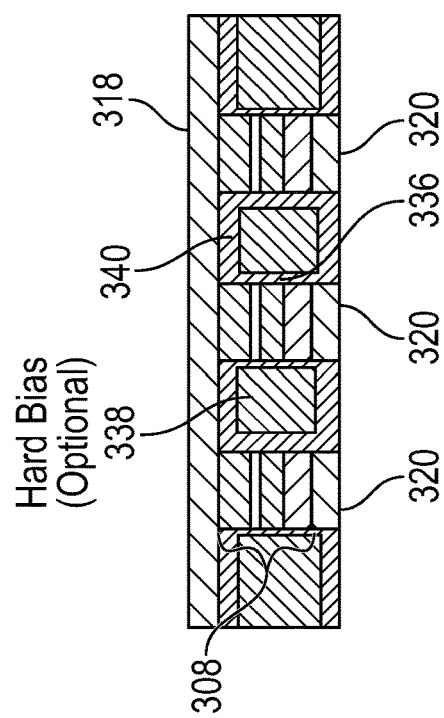

MAGNETORESISTIVE SENSOR ARRAY FOR MOLECULE DETECTION AND RELATED DETECTION SCHEMES

CROSS-REFERENCE TO RELATED APPLICATIONS

This application claims the benefit of and hereby incorporates by reference, for all purposes, the entirety of the contents of U.S. Provisional Application No. 62/833,237, filed Apr. 12, 2019 and entitled "MAGNETORESISTIVE SENSOR ELEMENTS FOR NUCLEIC ACID SEQUENCING ARRAYS AND DETECTION SCHEMES FOR NUCLEIC ACID SEQUENCING."

BACKGROUND

Field of the Disclosure

Embodiments of the present disclosure generally relate to magnetoresistive (MR) sensor arrays for detection of molecules coupled to magnetic nanoparticles (MNPs), such as for nucleic acid sequencing such as deoxyribonucleic acid (DNA) sequencing, and methods of using such MR sensor arrays for molecule detection.

Description of the Related Art

Current state-of-the-art sequencing systems are based on fluorescence signal detection and provide throughputs of 20 billion reads per run (https://www.illumina.com/systems/sequencing-platforms/novaseq.html). Achieving such performance requires large-area flow cells, high-precision free-space imaging optics, and expensive high-power lasers to generate sufficient fluorescence signals for successful base detection.

Gradual increases in sequencing by synthesis (SBS) throughput have been accomplished in two ways, the first being an outward scaling where the size and the number of flow cells in the sequencers is increased. This approach increases both the cost of reagents and the price of the sequencing system as more high-power lasers and high-precision nano-positioners must be employed. The second approach involves inward scaling where the density of DNA testing sites is increased so that the total number of sequenced DNA strands in a fixed-size flow cell is higher. To do so, increasingly higher numerical aperture (NA) lenses must be employed to distinguish the signal from neighboring fluorophores as the spacing decreases. However, this approach cannot be implemented indefinitely as the Rayleigh criterion puts the distance between resolvable light point sources at 0.61λ/NA, constraining the minimum distance between two sequenced DNA strands to be no smaller than ~400 nm. Similar resolution limits apply to sequencing directly on top of imaging arrays (similar to cell phone cameras) where the smallest pixel size achieved so far is ~1 μm (https://www.ephotozine.com/article/complete-guide-to-image-sensor-pixel-size-29652).

The Rayleigh criterion currently represents the fundamental limitation for inward scaling of optical SBS systems which can only be overcome by applying super-resolution imaging techniques (see A. M. Sydor, K. J. Czymmek, E. M. Puchner, and V. Mannella, "Super-Resolution Microscopy: From Single Molecules to Supramolecular Assemblies", Special Issue: Quantitative Cell Biology, Vol. 25, 730, 2015) and has not yet been achieved in highly multiplexed systems. Hence, increasing throughput and decreasing cost of optical SBS sequencers has been slow due to the need to build bigger flow cells and implement more expensive optical scanning and imaging systems.

Therefore, there is a need for new and improved apparatuses for and methods of detecting the presence of molecules such as nucleic acids that overcome the limitations of conventional apparatuses and methods.

SUMMARY

This summary represents non-limiting embodiments of the disclosure.

Disclosed herein are apparatuses and methods of using magnetic particles and magnetic sensors, such as magnetoresistive (MR) sensors, to perform molecule detection, such as for nucleic acid sequencing (e.g., DNA sequencing using SBS chemistry methods).

In some embodiments, a sensing device comprises at least one fluidic channel configured to receive a plurality of molecules to be detected, wherein at least some of the plurality of molecules are coupled to respective magnetic nanoparticles (MNPs), a plurality of magnetoresistive (MR) sensors, an insulating material encapsulating the plurality of MR sensors and for providing a barrier between the plurality of MR sensors and a contents of the at least one fluidic channel, and detection circuitry coupled to each of the plurality of MR sensors. In such embodiments, a surface of the insulating material within the fluidic channel provides a plurality of sites for binding the plurality of molecules to be sequenced, of the plurality of sites being located among the plurality of MR sensors, and the detection circuitry is configured to detect a characteristic of a magnetic noise of each of the plurality of MR sensors in response to a presence or absence of one or more magnetic nanoparticles (MNPs) at each of the plurality of sites, wherein the characteristic of the magnetic noise is influenced by the presence or absence of one or more MNPs at each of the plurality of sites. The characteristic of the magnetic noise may be an amplitude of the magnetic noise at a particular frequency or within a particular frequency band, a fluctuation of the magnetic noise, or a phase of the magnetic noise.

In some embodiments, one or more of the MR sensors comprises a pinned layer, a free layer, and a spacer layer disposed between the pinned layer and the free layer. The pinned layer or the free layer may comprise one or more ferromagnetic (FM) layers. The spacer layer may comprise an insulating layer or a metal layer, or both an insulating layer and a metal layer. In some embodiments, absent an applied magnetic field and absent the presence of one or more MNPs, an orientation of a magnetic moment of the free layer is approximately 90° from an orientation of a magnetic moment of the pinned layer.

In some embodiments in which the characteristic of the magnetic noise is an amplitude of the magnetic noise at a particular frequency or within a particular frequency band, the detection circuitry comprises a bias element coupled to at least one of the plurality of MR sensors and configured to generate a bias across the at least one of the plurality of MR sensors, a first low pass filter and amplifier combination coupled to the at least one of the plurality of MR sensors to filter and amplify a signal from the at least one of the plurality of MR sensors, a reference oscillator configured to generate a reference signal having a particular frequency chosen to maximize a change in the signal at the particular frequency when at least one of the one or more MNPs labeling a particular molecule type is detected by the at least one of the plurality of MR sensors at one or more of the plurality of sites, a mixer coupled to the reference oscillator and an output of the first low pass filter and amplifier combination, wherein the mixer is configured to mix an output signal from the first low pass filter and amplifier combination with the reference signal, a second low pass filter and amplifier combination coupled to the mixer, and an envelope detector configured to receive an output signal from the second low pass filter and amplifier combination and provide a signal for detection, wherein a voltage of the signal for detection is proportional to the amplitude of the magnetic noise.

In some embodiments in which the characteristic of the magnetic noise is a fluctuation of the magnetic noise, the detection circuitry comprises a bias element coupled to at least one of the plurality of MR sensors and configured to generate a bias across the at least one of the plurality of MR sensors, an amplifier coupled to the at least one of the plurality of MR sensors to filter and amplify a signal from the at least one of the plurality of MR sensors, a filter coupled to the amplifier, and an envelope detector configured to receive an output signal from the filter and provide a signal for detection, wherein a voltage of the signal for detection is proportional to the fluctuation of the magnetic noise.

In some embodiments in which the characteristic of the magnetic noise is a phase of the magnetic noise, the detection circuitry comprises a phase locked loop configured to provide an error signal output that corresponds to the phase of the magnetic noise.

In some embodiments, the sensing device further comprises a plurality of lines coupled to the plurality of MR sensors, and a plurality of selector elements, each of the plurality of selector elements coupled to at least one of the plurality of lines and to a respective one of the plurality of MR sensors. In some embodiments, the plurality of selector elements comprises a transistor. In some embodiments, the plurality of selector elements comprises an in-stack selector element.

In some embodiments, the sensing device is a sequencing device, and the molecules are biologic molecules (e.g., nucleic acid molecules).

In some embodiments, a first subset of the plurality of MR sensors is arranged in a first row, a second subset of the plurality of MR sensors is arranged in a second row, the second row being substantially parallel to the first row, and the at least one fluidic channel is disposed between the first and second rows.

In some embodiments, the sensing device further comprises a selector element, such as a transistor or an in-stack selector element.

In some embodiments, the sensing device further comprises a magnetic component configured to apply a magnetic field across the sensing device. The magnetic component may be, for example, an electromagnet, a distributed coil, a solenoid, a permanent magnet, a super-conducting magnet, or a combination thereof.

In some embodiments, a method of using the sensing device comprises applying a magnetic field across the sensing device, and detecting, by the detection circuitry, the characteristic of the magnetic noise of each of the plurality of MR sensors. In some such embodiments, in a vicinity of each of the plurality of MR sensors, the applied magnetic field is (a) in a substantially same direction as a field emanating from the one or more MNPs, or (b) in a substantially opposite direction from the field emanating from the one or more MNPs.

In some embodiments, at least one of the MR sensors comprises a pinned layer, a free layer, and a spacer layer disposed between the pinned layer and the free layer, and an orientation of a magnetic moment of the free layer is approximately 90° from an orientation of a magnetic moment of the pinned layer, and a method of fabricating the sensing device comprises at least one of: applying a hard bias field; patterning the at least one of the MR sensors into a rectangle or ellipse; etching the free and pinned layers along an axis to induce texturing; or using perpendicular magnetic anisotropy to pull the free layer out of plane while keeping the pinned layer in the plane of the at least one of the MR sensors.

In some embodiments, a sensing device comprises at least one fluidic channel configured to receive a plurality of molecules to be detected, wherein at least some of the plurality of molecules to be detected are coupled to respective magnetic nanoparticles (MNPs), a plurality of magnetoresistive (MR) sensors, an insulating material encapsulating the plurality of MR sensors and for providing a barrier between the plurality of MR sensors and a contents of the at least one fluidic channel, and detection circuitry coupled to each of the plurality of MR sensors. In some such embodiments, a surface of the insulating material within the fluidic channel provides a plurality of sites for binding the plurality of molecules to be detected, the plurality of sites being located among the plurality of MR sensors, and the detection circuitry is configured to detect a change in resistance, current, and/or voltage drop across each of the plurality of MR sensors, wherein the change in resistance, current, and/or voltage drop is influenced by the presence or absence of one or more MNPs at each of the plurality of sites.

In some embodiments, the detection circuitry is further configured to report the change in resistance, current, and/or voltage drop as a binary output that indicates the presence or absence of a particular MNP labeling a particular molecule type at each of the plurality of sites.

In some embodiments, the detection circuitry is further configured to report the change in resistance, current, or voltage drop at each of the plurality of sites as a quantized output having one of a plurality of levels, at least some of the levels being used to differentiate MNPs having different saturation magnetizations, with each saturation magnetization corresponding to a particular MNP labeling a particular molecule type.

In some embodiments, the sensing device further comprises a plurality of lines coupled to the plurality of MR sensors, and a plurality of selector elements, each of the plurality of selector elements coupled to at least one of the plurality of lines and to a respective one of the plurality of MR sensors. In some embodiments, the plurality of selector elements includes a transistor. In some embodiments, the plurality of selector elements is an in-stack selector element.

In some embodiments, the sensing device is a sequencing device, and the molecules are biologic molecules (e.g., nucleic acid molecules).

In some embodiments, each of the MR sensors comprises a pinned layer, a free layer, and a spacer layer disposed between the pinned layer and the free layer, and, absent an applied magnetic field and absent the presence of one or more MNPs, an orientation of a magnetic moment of the free layer is approximately 90° from an orientation of a magnetic moment of the pinned layer.

In some embodiments, a first subset of the plurality of MR sensors is arranged in a first row, a second subset of the plurality of MR sensors is arranged in a second row, the second row being substantially parallel to the first row, and the at least one fluidic channel is disposed between the first and second rows.

In some embodiments, the sensing device further comprises a selector element. In some embodiments, the selector element comprises a transistor. In some embodiments, the selector element is an in-stack selector element.

In some embodiments, at least one of the MR sensors comprises a pinned layer, a free layer, and a spacer layer disposed between the pinned layer and the free layer, and an orientation of a magnetic moment of the free layer is approximately 90° from an orientation of a magnetic moment of the pinned layer, and a method of fabricating the sensing device comprises at least one of: applying a hard bias field; patterning the at least one of the MR sensors into a rectangle or ellipse; etching the free and pinned layers along an axis to induce texturing; or using perpendicular magnetic anisotropy to pull the free layer out of plane while keeping the pinned layer in the plane of the at least one of the MR sensors.

BRIEF DESCRIPTION OF THE DRAWINGS

So that the manner in which the above-recited features of the present disclosure can be understood in detail, a more particular description of the disclosure is provided in reference to embodiments, some of which are illustrated in the appended drawings. It is to be noted, however, that the appended drawings illustrate only typical embodiments of this disclosure and are therefore not to be considered limiting of its scope, for the disclosure may admit to other equally-effective embodiments. Objects, features, and advantages of the disclosure will be readily apparent from the following description of certain embodiments taken in conjunction with the accompanying drawings in which:

FIGS. 8A, 8B, and 8C illustrate a cross-point array architecture of MR sensor elements in accordance with some embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
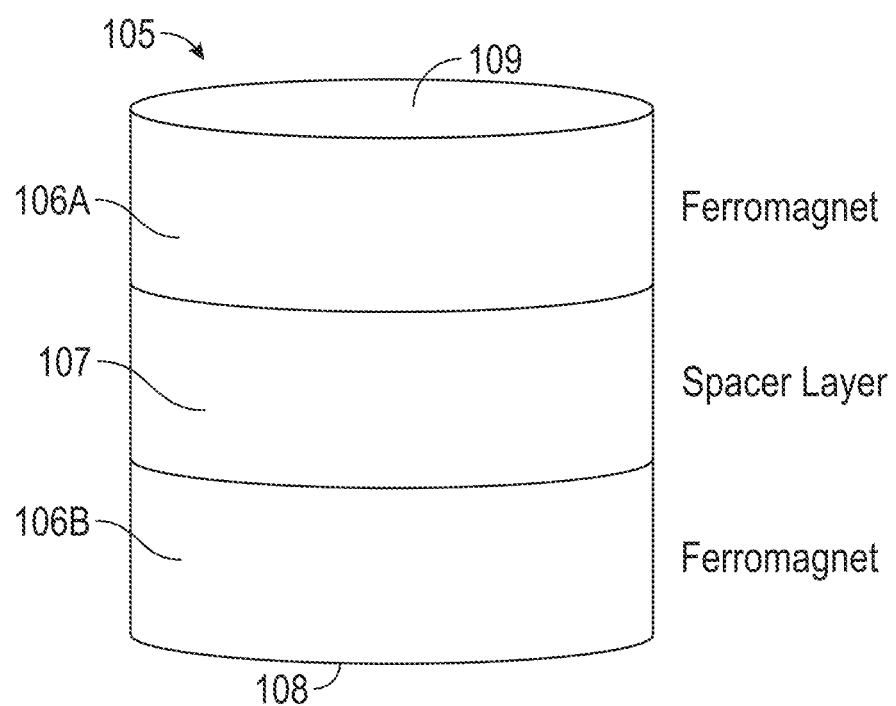
FIG. 1 illustrates a portion of a magnetic sensor in accordance with some embodiments.

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

The terms "over," "under," "between," "on," and other similar terms as used herein refer to a relative position of one layer with respect to other layers. As such, for example, one layer disposed over or under another layer may be directly in contact with the other layer or may have one or more intervening layers. Moreover, one layer disposed between layers may be directly in contact with the two layers or may have one or more intervening layers. In contrast, a first layer "on" a second layer is in contact with the second layer. The relative position of the terms does not define or limit the layers to a vector space orientation of the layers.

The term "coupled" is used herein to refer to elements that are either directly connected or connected through one or more intervening elements. For example, as explained below a line (e.g., for selecting or reading a characteristic of a magnetic sensor) may be directly connected to a magnetic sensor, or it may be connected via intervening elements.

It is to be understood that the disclosures herein may be used to detect any type of molecule to which a magnetic particle can be attached. In other words, any molecule type that can be labeled by a magnetic nanoparticle may be detected using the sensing devices disclosed herein. Such molecule types may be biologic molecule types, such as proteins, antibodies, etc. For example, the disclosures herein may be used to detect nucleic acids (e.g., in DNA sequencing). The disclosures herein may also be used to detect non-biologic (inorganic or non-living) molecules, such as contaminants, minerals, chemical compounds, etc. The presentation of the disclosure in the context of nucleic acid sequencing is solely exemplary and is not intended to limit the scope of the present disclosure.

Furthermore, although the description herein focuses on DNA as an exemplary nucleic acid, the various embodiments described can be applied to nucleic acid sequencing in general. Similarly, although SBS is used for illustrative purposes in the following description, the various embodiments are not so limited to SBS sequencing protocols (e.g., dynamic sequencing could be used instead).

Disclosed herein are apparatuses and methods to use magnetic particles and magnetic sensors to perform detection of molecules, such as in nucleic acid sequencing (e.g., DNA sequencing using SBS chemistry methods). Specifically, embodiments of this disclosure are directed to various magnetoresistive (MR) device embodiments that can be used as magnetic field detectors. Embodiments of the present disclosure also include various detection methods to measure characteristics of the magnetic sensors and/or variations in the magnetic sensor characteristics in response to a magnetic field from a magnetic nanoparticle label.

In some embodiments, an apparatus for molecule detection comprises an array of magnetic sensors. Each of the magnetic sensors of the magnetic sensor array may be a thin-film device that uses the MR effect (e.g., it may be a MR sensor) to detect magnetic nanoparticles (MNPs) in a fluidic channel of the apparatus. Each magnetic sensor may operate as a potentiometer with a resistance that varies as the strength and/or direction of the sensed magnetic field changes. Each magnetic sensor may have dimensions of less than about 30 nm to detect magnetic fields on the order of a few millitesla (mT).

FIG. 1 illustrates a portion of a magnetic sensor 105 in accordance with some embodiments. The exemplary magnetic sensor 105 of FIG. 1 has a bottom portion 108 and a top portion 109 and comprises three layers, e.g., two ferromagnetic layers 106A, 106B separated by a nonmagnetic spacer layer 107. The nonmagnetic spacer layer 107 may be, for example, a metallic material or combination of metallic materials, such as, for example, copper or silver, in which case the structure is called a spin valve (SV), or it may be an insulator such as, for example, alumina or magnesium oxide, in which case the structure is referred to as a magnetic tunnel junction (MTJ). Suitable materials for use in the ferromagnetic layers 106A, 106B include, for example, alloys of Co, Ni, and Fe (sometimes mixed with other elements). The example materials described above are merely exemplary and are not intended to be limiting. Materials suitable for use in MTJs are known to those having ordinary skill in the art.

In some embodiments, the magnetic sensor 105 is a thin-film device, and the ferromagnetic layers 106A, 106B are engineered to have their magnetic moments oriented either substantially in the plane of the film or substantially perpendicular to the plane of the film. Additional materials may be deposited below and/or above the three layers 106A, 106B, and 107 shown in FIG. 1 to serve purposes such as interface smoothing, texturing, and protection from processing used to pattern the apparatus 100 (shown and described in the context of, e.g., FIGS. 4A, 5A, etc.), but the active region of the magnetic sensor 105 lies in the trilayer structure shown in FIG. 1. Thus, a component that is in contact with a magnetic sensor 105 may be in contact with one of the three illustrated layers 106A, 106B, or 107, or it may be in contact with another part of the magnetic sensor 105 that is not illustrated in FIG. 1.

Figure 2A:
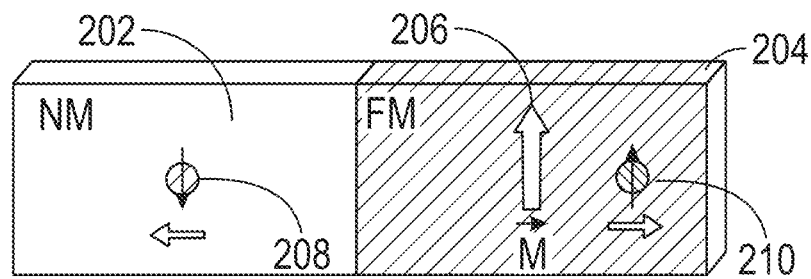
FIGS. 2A, 2B, and 2C illustrate the basic construction of a magnetoresistive (MR) device and how it can be used as a magnetic sensor in accordance with some embodiments.

To understand how a MR device works, consider how an electron in an electric current interacts with a thin film ferromagnetic (FM) layer. Quantum mechanics dictate that the probability is high that an electron interacting with the FM layer will cause the electron spin to be oriented preferentially parallel or antiparallel to the direction of the magnet's moment for transmitted and reflected electrons respectively, as shown in FIG. 2A. Electrons with spin parallel to the moment 206 of the FM layer 204 preferentially pass through the FM layer 204 (spin 210), whereas those with spin antiparallel preferentially are reflected back (spin 208). Due to this phenomenon, the interface between a nonmagnetic (NM) layer 202 (assumed for purposes of this explanation to be a metal layer) and a FM layer 204 acts as a spin filter that can act to spin polarize (i.e., make one spin direction more preferential) an incoming electric current.

Figure 2B:
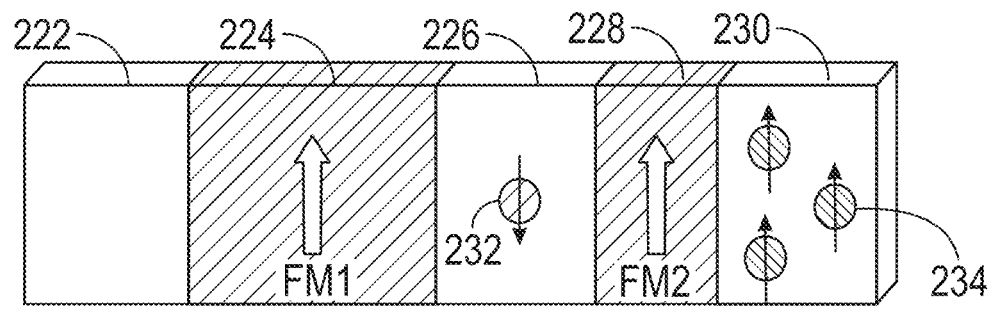
Figure 2C:
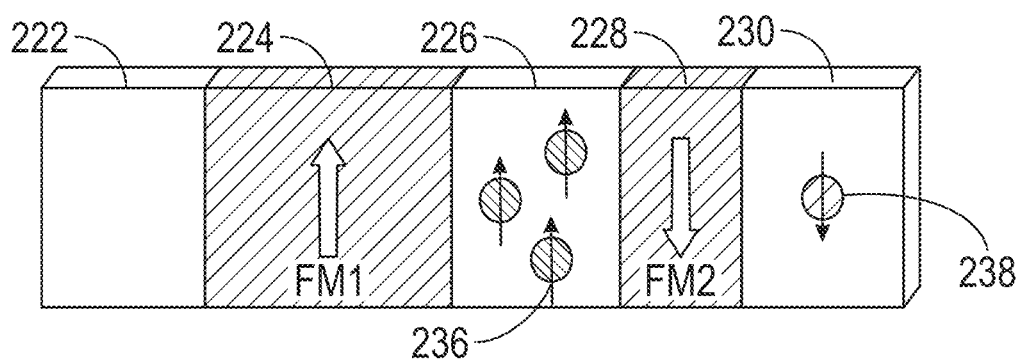

For a device with two FM layers 224 and 228 separated by a nonmagnetic metal layer 226 (spacer layer) as shown in FIGS. 2B and 2C, an incoming electric current spin polarized by the first FM layer (FM1) 224 interacts differently with the second FM layer (FM2) 228, depending on the orientation of that layer's magnetic moment. If the moments of both FM layers 224 and 228 are parallel to one another (FIG. 2B), then many electrons will pass through the device because many electrons in the current will have their spin oriented with the moment of the second FM 228 (spin 234). Few electrons will be reflected back (spin 232).

In the opposite case, where the moments of the two FM layers 224 and 228 are oriented in an anti-parallel fashion (FIG. 2C), many electrons will be blocked from passing through the second FM layer 228 (spin 236), and far fewer electrons will traverse the device (spin 238). This means the amount of current passing through the device is dependent on the orientation of the two FM layers 224 and 228 with respect to one another. Because the resistance of the device is proportional to the current, the resistance of the device is dependent on the orientation of the moments (i.e., the resistance is smaller when the moments are parallel than it is when they are antiparallel).

Whereas the above description presumes use of a nonmagnetic metal spacer layer 226 separating the two FM layers 224 and 228, (a configuration also known as a spin valve (SV) or giant magnetoresistance (GMR) device), an insulating layer known as a tunneling barrier can alternatively be used as the spacer layer separating the FM layers. In such implementations, the spacer layer may be made of oxide-based material. These types of devices are called magnetic tunnel junctions (MTJs), and they exhibit a similar resistance response (referred to as tunnel magnetoresistance or TMR) because of spin polarized tunneling as opposed to spin filtering.

MR devices have been used in many applications, including magnetic recording, magnetic field sensing, and magnetic memory. In these cases, it is usually preferable to design the MR device to have one FM layer be effectively "pinned" so that the direction in which its moment points in stays fixed and is not easily altered by the application of a magnetic field. This is usually achieved by placing an antiferromagnetic (AFM) layer adjacent to the pinned layer and using an effect called exchange coupling that provides strong unidirectional anisotropy for the FM layer's moment. The second FM layer is left "free" to rotate under the impulse of a magnetic field such that its moment rotates with respect to the fixed orientation of the pinned FM layer so that the resistance of the device becomes a detector of the magnetic field direction or amplitude by effectively acting as a magnetic field to voltage transducer.

Magnetoresistance can be defined as $$MR = R_0 + \Delta R \sin^2\left(\frac{\theta}{2}\right),$$

where $R_0$ is the resistance of the device when the moments are oriented in a parallel configuration, $\Delta R$ is the difference between resistance in parallel and antiparallel orientations, and $\theta$ is the angle between the two moments. For magnetic field sensing applications, a linear response to the magnetic field is desired from the sensor. Considering the equation above, the sensor should ideally be designed and fabricated to have the two FM layers oriented approximately 90° with respect to one another. This may be achieved by exchange biasing the pinned layer with an anti-ferromagnet and using a "hard bias" coating to rotate the free layer approximately 90° away from the pinned layer. Further detail on this design, as applied to embodiments related to sequencing applications, will be given below.

Figure 3A:
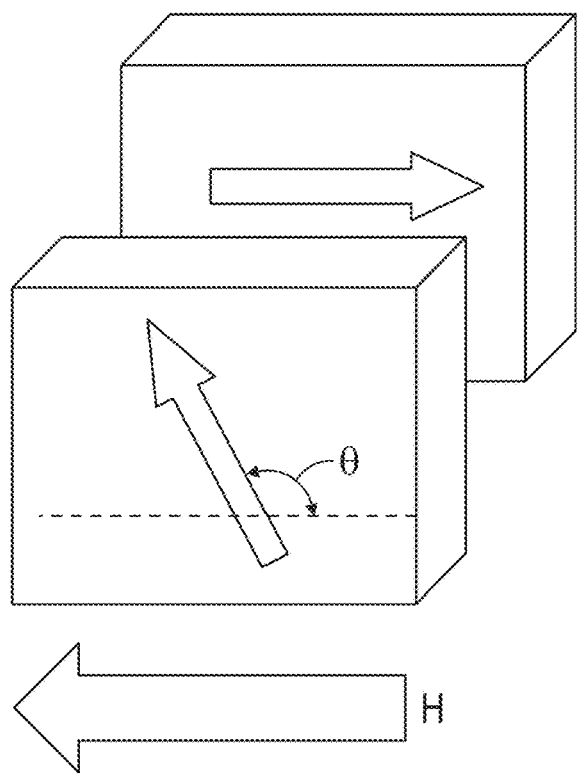
FIGS. 3A and 3B illustrate the relationship between the resistance of the exemplary magnetic sensor illustrated in FIG. 1 and the angle between the moments of its two ferromagnetic layers in accordance with some embodiments.
Figure 3B:
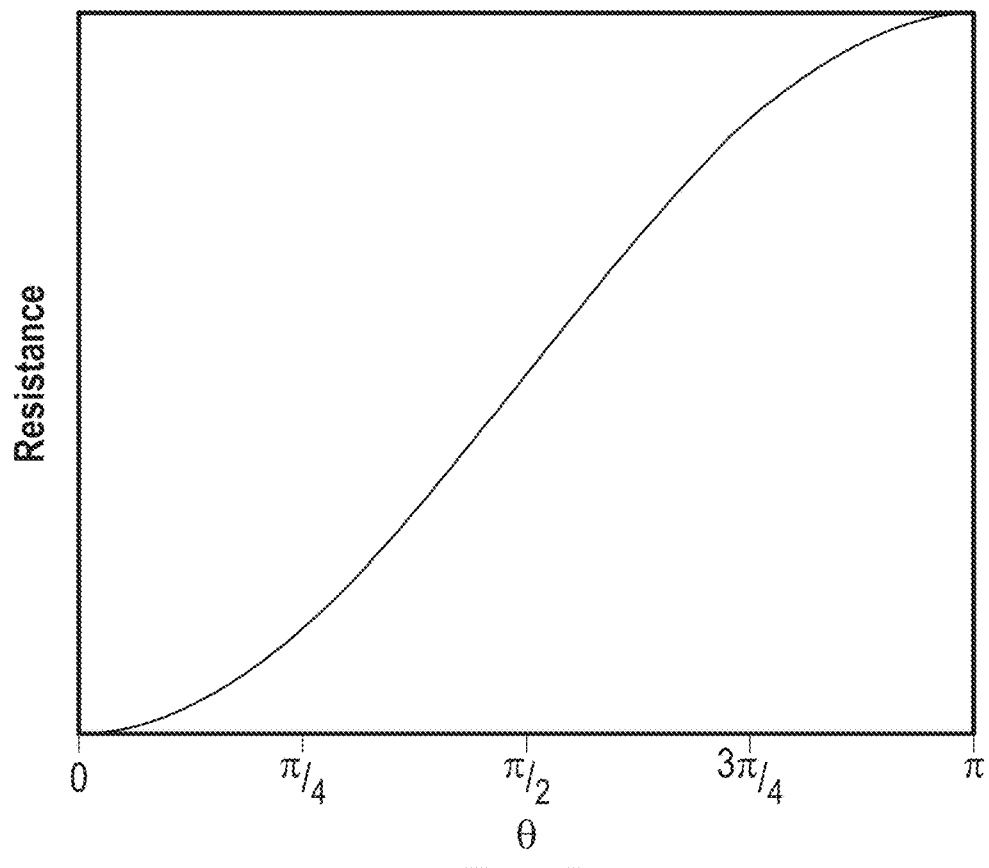

FIGS. 3A and 3B illustrate the resistance of MR sensors, which is proportional to 1-cos($\theta$), where $\theta$ is the angle between the moments of the two ferromagnetic layers 106A, 106B shown in FIG. 1. To maximize the signal generated by a magnetic field and provide a linear response of the magnetic sensor 105 to an applied magnetic field, the magnetic sensors 105 may be designed such that the moments of the two ferromagnetic layers 106A, 106B are oriented $\pi/2$ or 90 degrees with respect to one another in the absence of a magnetic field. This orientation can be achieved by any number of methods that are known in the art. As discussed above, one solution is to use an antiferromagnet to "pin" the magnetization direction of one of the ferromagnetic layers (either 106A or 106B, designated as "FM1") through an effect called exchange biasing and then coat the sensor with a bilayer that has an insulating layer and permanent magnet. The insulating layer avoids electrical shorting of the magnetic sensor 105, and the permanent magnet supplies a "hard bias" magnetic field perpendicular to the pinned direction of FM1 that will then rotate the second ferromagnet (either 106B or 106A, designated as "FM2") and produce the desired configuration. Magnetic fields parallel to FM1 then rotate FM2 about this 90 degree configuration, and the change in resistance results in a voltage signal that can be calibrated to measure the field acting upon the magnetic sensor 105. In this manner, the magnetic sensor 105 acts as a magnetic-field-to-voltage transducer.

Note that although the example discussed immediately above described the use of ferromagnets that have their moments oriented in the plane of the film at 90 degrees with respect to one another, a perpendicular configuration can alternatively be achieved by orienting the moment of one of the ferromagnetic layers 106A, 106B substantially out of the plane of the film, which may be accomplished using what is referred to as perpendicular magnetic anisotropy (PMA).

Figure 4A:
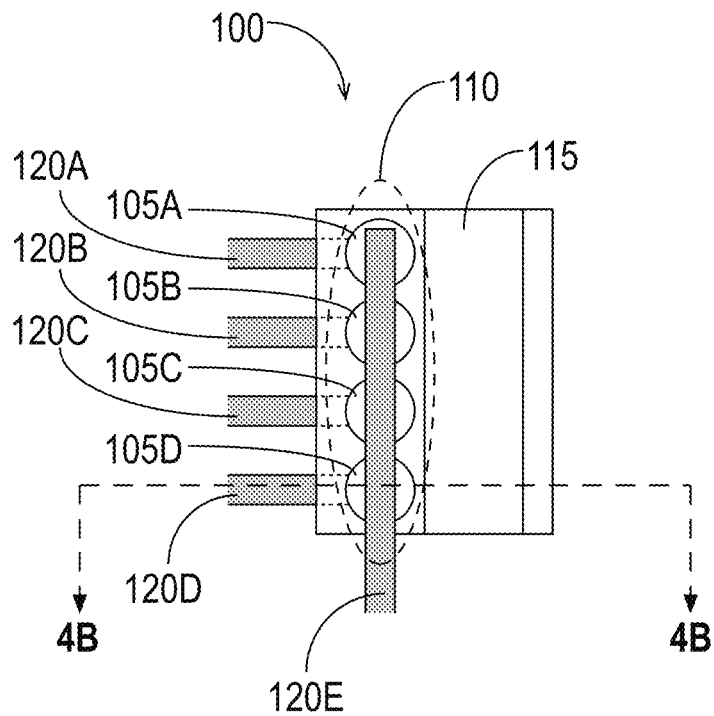
FIGS. 4A, 4B, and 4C illustrate an apparatus for molecule detection in accordance with some embodiments.
Figure 4B:
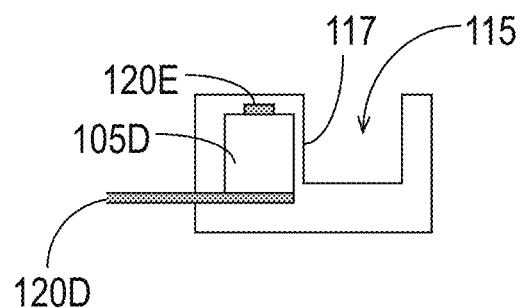
Figure 4C:
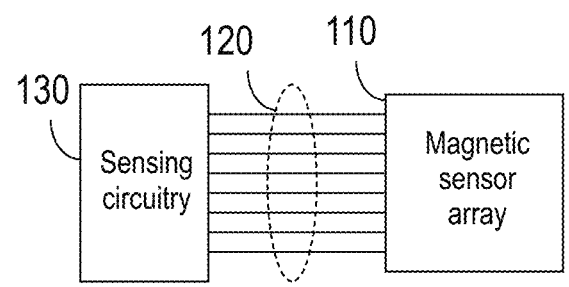

The magnetic sensors 105 may be incorporated into an apparatus for the detection of molecules that are coupled to respective magnetic nanoparticles (e.g., for nucleic acid sequencing). FIGS. 4A, 4B, and 4C illustrate an apparatus 100 that may be used, e.g., for nucleic acid sequencing in accordance with some embodiments. FIG. 4A is a top view of the apparatus, and FIG. 4B is a cross-section view at the position indicated in FIG. 4A. FIG. 4C is a block diagram showing components of the apparatus 100. As shown in FIGS. 4A and 4C, the apparatus 100 comprises a magnetic sensor array 110 that includes a plurality of magnetic sensors 105, with four magnetic sensors 105A, 105B, 105C, and 105D shown in FIG. 4A. (For simplicity, this document refers generally to the magnetic sensors by the reference number 105. Individual magnetic sensors are given the reference number 105 followed by a letter.) The magnetic sensor array 110 shown in the exemplary embodiment of FIG. 4A is a linear array.

In some embodiments, each of the plurality of magnetic sensors 105 is coupled to at least one line 120 for reading a characteristic of one or more of the magnetic sensors 105 (e.g., an amplitude of the magnetic noise at a particular frequency or within a particular frequency band, a fluctuation of the magnetic noise, a phase of the magnetic noise, and/or a change in resistance, current, and/or voltage drop across the magnetic sensor 105). (For simplicity, this document refers generally to the lines by the reference number 120. Individual lines are given the reference number 120 followed by a letter.) In the exemplary embodiment shown in FIG. 4A, each magnetic sensor 105 of the magnetic sensor array 110 is coupled to two lines 120. Specifically, the magnetic sensor 105A is coupled to the lines 120A and 120E, the magnetic sensor 105B is coupled to the lines 120B and 120E, the magnetic sensor 105C is coupled to the lines 120C and 120E, and the magnetic sensor 105D is coupled to the lines 120D and 120E. The lines 120A, 120B, 120C, and 120D reside under the magnetic sensors 105A, 105B, 105C, and 105D, respectively, and the line 120E resides over the magnetic sensors 105. FIG. 4B shows the magnetic sensor 105D in relation to the lines 120D and 120E.

The apparatus 100 also includes a fluidic channel 115 (also referred to herein as a nanochannel) that is adjacent to the magnetic sensor array 110. As its name suggests, the fluidic channel 115 is configured to hold fluids (e.g., liquids, gases, plasmas) when the apparatus 100 is in use. The fluidic channel 115 may by open (e.g., if its shape is rectangular, it may have three sides; if its shape is curved, it may have a shape that is a portion of a cylinder; etc.) or closed (e.g., if its shape is rectangular, it may have four sides; if its shape is curved, it may be cylindrical; etc.). The shape of the fluidic channel 115 may be regular or irregular. The fluidic channel 115 may be coupled to a pump that forces fluids into the fluidic channel 115. Alternatively, the fluidic channel 115 may be passive (e.g., it merely receives fluids but is not coupled to a device that injects or removes fluids).

The fluidic channel 115 has a wall 117 that is adjacent to the magnetic sensor array 110. The wall 117 may be referred to as a proximal wall. The wall 117 may be substantially vertical as illustrated in FIG. 4B. Alternatively, the wall 117 may be sloped at least in part (e.g., some or all of the interior of the fluidic channel 115 may be curved (e.g., in the shape of a portion or all of a cylinder)). In general, the fluidic channel 115 and wall 117 may have any shapes that allow the magnetic sensors 105 to detect the presence of magnetic particles on the other side of the wall 117, within the fluidic channel 115.

When the apparatus 100 is in use, the magnetic sensors 105 are able to detect, through the wall 117, magnetic nanoparticles (MNPs) that are in the fluidic channel 115. Thus, the wall 117 has properties and characteristics that protect the magnetic sensors 105 from whatever fluid is in the fluidic channel 115 while still allowing the magnetic sensors 105 to detect MNPs that are within the fluidic channel 115. For example, the material of the wall 117 (and potentially of the rest of the fluidic channel 115) may be or comprise an insulator. For example, in some embodiments, a surface of the wall 117 comprises polypropylene, gold, glass, and/or silicon. In addition, the thickness of the wall 117 may be selected so that the magnetic sensors 105 can detect MNPs within the fluidic channel 115. In some embodiments, the wall 117 is approximately 2 nm to approximately 20 nm thick.

In some embodiments, the wall 117 has a structure (or multiple structures) configured to anchor molecules to be sensed (e.g., nucleic acid or molecules of a nucleic acid polymerase) to the wall 117. For example, the structure (or structures) of the wall 117 may include a cavity or a ridge.

To simplify the explanation, FIGS. 4A and 4B illustrate an exemplary apparatus 100 with a single fluidic channel 115 and only four magnetic sensors 105A, 105B, 105C, 105D in the magnetic sensor array 110. It is to be appreciated that the apparatus 100 may have many more magnetic sensors 105 in the magnetic sensor array 110, and it may have either additional fluidic channels 115 or a more intricate single fluidic channel 115 (e.g., with a different shape or with interconnected channels). In general, any configuration of magnetic sensors 105 and fluidic channel(s) 115 that allows the magnetic sensors 105 to detect MNPs in the fluidic channel(s) 115 may be used.

As illustrated in FIG. 4C, the apparatus 100 includes sensing circuitry 130 coupled to the magnetic sensor array 110 via the lines 120. In some embodiments, in operation, the sensing circuitry 130 applies a current to the lines 120 to detect a characteristic of at least one of the plurality of magnetic sensors 105 in the magnetic sensor array 110, where the characteristic indicates a presence or an absence of a magnetically-labeled nucleotide precursor in the fluidic channel 115. For example, in some embodiments, the characteristic is a magnetic field or a resistance, or a change in magnetic field or a change in resistance, current, and/or voltage drop. In some embodiments, the characteristic is a magnetic noise, a noise level, a noise jitter, and/or a noise variance.

As an example of an apparatus 100 with a larger number of magnetic sensors 105 in the magnetic sensor array 110, FIGS. 5A, 5B, 5C, and 5D illustrate portions of an exemplary apparatus 100 that includes several channels, one or more of which may be a separate fluidic channel 115 in accordance with some embodiments, or the aggregation of which may be considered a single fluidic channel 115. In the embodiment of the apparatus 100 shown in FIGS. 5A, 5B, 5C, and 5D, the plurality of magnetic sensors 105 of the magnetic sensor array 110 is arranged in a rectangular grid pattern. Each of the lines 120 identifies a row or a column of the magnetic sensor array 110. It is to be understood that FIGS. 5A, 5B, 5C, and 5D show only a portion of the apparatus 100 to avoid obscuring the parts of the apparatus 100 being discussed. It is to be understood that the various illustrated components (e.g., lines 120, magnetic sensors 105, fluidic channels 115, etc.) might not be visible in a physical instantiation of the apparatus 100 (e.g., some or all may be covered by protective material, such as an insulator).

Figure 5A:
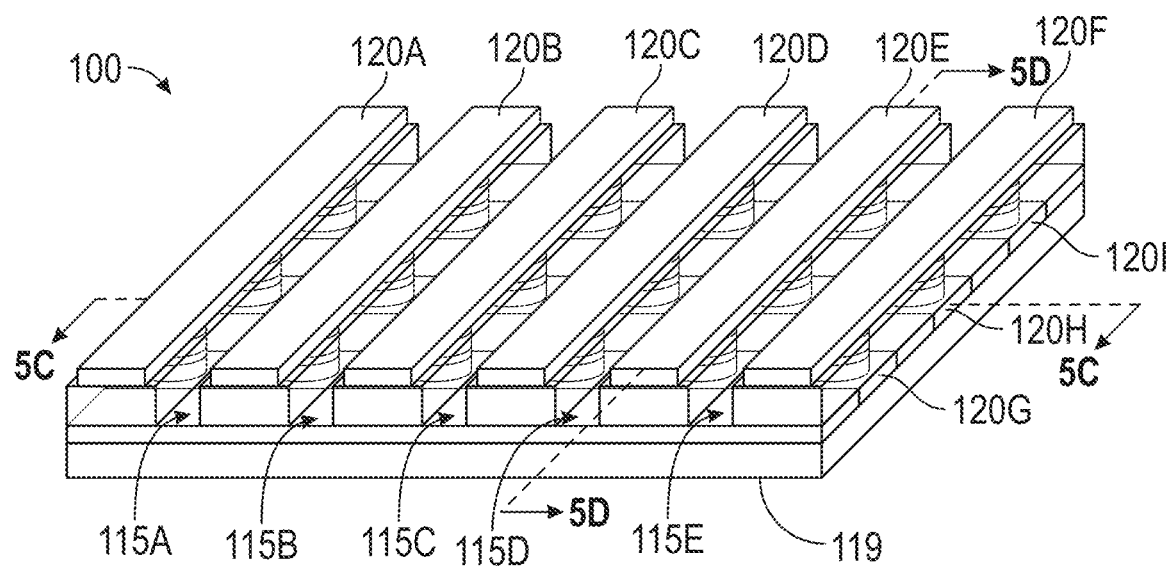
FIGS. 5A, 5B, 5C, and 5D illustrate portions of an exemplary apparatus that includes several channels in accordance with some embodiments.

FIG. 5A is a perspective view of the exemplary apparatus 100 in accordance with some embodiments. The apparatus 100 includes nine lines 120, labeled as 120A, 120B, 120C, 120D, 120E, 120F, 120G, 120H, and 120I. It also includes five fluidic channels, labeled as 115A, 115B, 115C, 115D, and 115E. As explained above, the fluidic channels 115A, 115B, 115C, 115D, and 115E may be considered to be separate fluidic channels 115 or a single fluidic channel 115. The apparatus 100 also has a bottom surface 119.

Figure 5B:
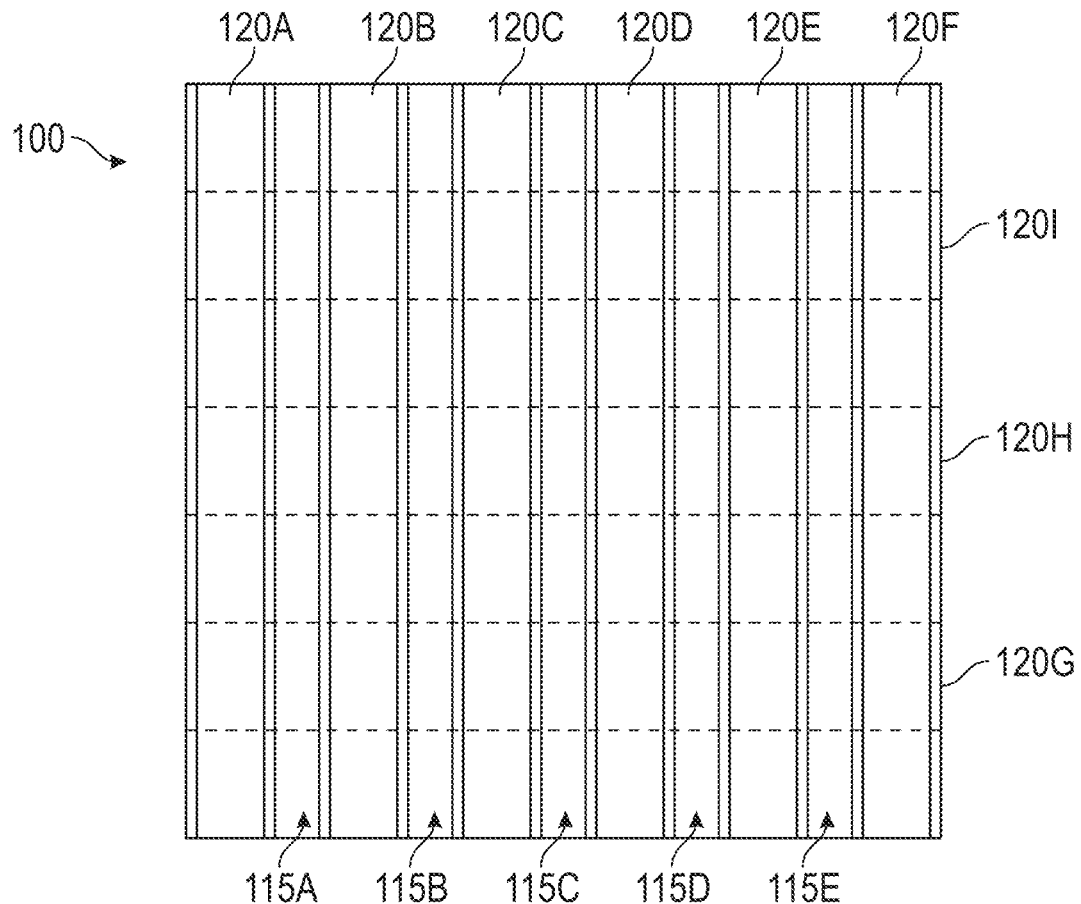

FIG. 5B is a top view of the exemplary apparatus 100 from FIG. 5A. The lines 120G, 120H, and 120I, which are not visible from the top view, are shown using dashed lines to indicate their locations. The lines 120A-120F are shown in solid lines but, as explained above, the lines 120A-120F might also not be visible in the top view (e.g., they may be covered by protective material, such as an insulator).

Figure 5C:
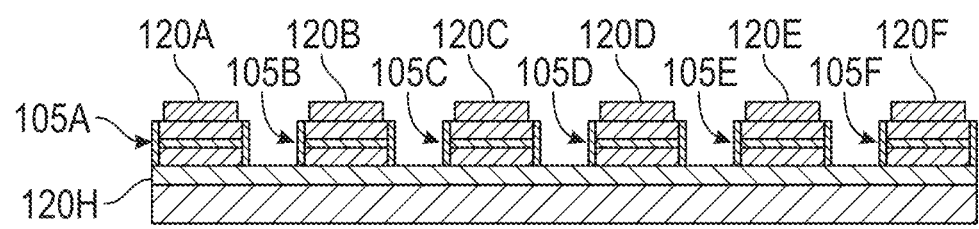

FIG. 5C is a cross-sectional view of the apparatus 100 along the line labeled "5C" in FIG. 5A. As shown, each of the lines 120A, 120B, 120C, 120D, 120E, and 120F is in contact with the top of one of the magnetic sensors 105 along the cross-section (namely, line 120A is in contact with magnetic sensor 105A, line 120B is in contact with magnetic sensor 105B, line 120C is in contact with magnetic sensor 105C, line 120D is in contact with magnetic sensor 105D, line 120E is in contact with magnetic sensor 105E, and line 120F is in contact with magnetic sensor 105F). The line 120H is in contact with the bottom of each of the magnetic sensors 105A, 105B, 105C, 105D, 105E, and 105F. It is to be appreciated that although FIGS. 5A-5D illustrate the lines 120 in contact with the magnetic sensors 105, the lines 120 may, in general, be coupled to the magnetic sensors 105 (i.e., they may be directly connected, or there may be intervening components disposed between the lines 120 and the magnetic sensors 105).

The magnetic sensors 105A and 105B are separated by the fluidic channel 115A (unlabeled in FIG. 5C but shown in FIG. 5A). Similarly, the magnetic sensors 105B and 105C are separated by the fluidic channel 115B, the magnetic sensors 105C and 105D are separated by the fluidic channel 115C, the magnetic sensors 105D and 105E are separated by the fluidic channel 115D, and the magnetic sensors 105E and 105F are separated by the fluidic channel 115E. As discussed further below, either or both of the vertical walls of each fluidic channel 115 may be the wall 117.

In some embodiments, each magnetic sensor 105 is assigned to a single fluidic channel 115. For example, in the exemplary device illustrated in FIGS. 5A-5D, the magnetic sensors 105 coupled to the line 120A may be configured to sense MNPs in the fluidic channel 115A, the magnetic sensors 105 coupled to the line 120B may be configured to sense MNPs in the fluidic channel 115B, the magnetic sensors 105 coupled to the line 120C may be configured to sense MNPs in the fluidic channel 115C, the magnetic sensors 105 coupled to the line 120D may be configured to sense MNPs in the fluidic channel 115D, and the magnetic sensors 105 coupled to the line 120E may be configured to sense MNPs in the fluidic channel 115E.

In the exemplary embodiment illustrated in FIGS. 5A-5C, there are more columns of magnetic sensors 105 than there are fluidic channels 115 (i.e., in the exemplary embodiment shown, there are six columns corresponding to lines 120A-120F and only five fluidic channels 115A-115E). In such embodiments, each vertical wall of one fluidic channel 115 may be the wall 117. In other words, a single fluidic channel 115 may be sensed by twice as many magnetic sensors 105 as each of the other fluidic channels 115. For example, in the exemplary embodiment of FIGS. 5A-5D, any of the fluidic channels 115 may be sensed by two columns of magnetic sensors 105. For example, the fluidic channel 115B may be sensed by the magnetic sensors 105 coupled to both lines 120B and 120C. In this example, the magnetic sensors 105 coupled to the line 120A would be assigned to sense the contents of the fluidic channel 115A 120A, the magnetic sensors 105 coupled to the line 120D would be assigned to sense the contents of the fluidic channel 115C, the magnetic sensors 105 coupled to the line 120E would be assigned to sense the contents of the fluidic channel 115D, and the magnetic sensors 105 coupled to the line 120F would be assigned to sense the contents of the fluidic channel 115E.

Figure 5D:
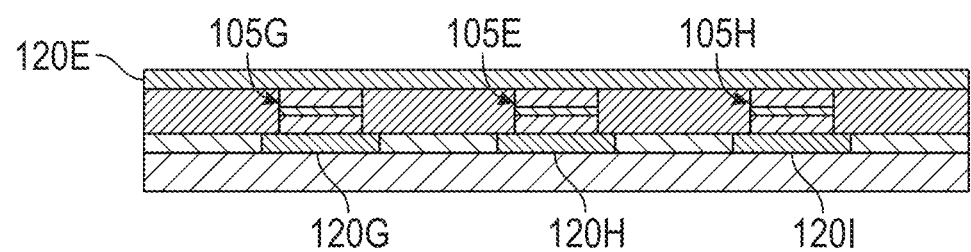

FIG. 5D is a cross-sectional view of the apparatus 100 along the line labeled "5D" in FIG. 5A. As shown, the line 120E is in contact with the top of each of the sensors 105G, 105E, and 105H along the cross-section. Each of the lines 120G, 120H, and 120I is in contact with the bottom of one of the magnetic sensors 105 along the cross-section (namely, line 120G is in contact with magnetic sensor 105G, line 120H is in contact with magnetic sensor 105E, and line 120I is in contact with magnetic sensor 105H). As explained above, the lines 120 shown in FIG. 5D need not be in direct contact with the magnetic sensors 105; instead, they may be connected through intervening components.

In some embodiments (see, e.g., FIGS. 5E, 5F), the apparatus 100 includes a plurality of selector elements 111, each of which is coupled to a respective one of the magnetic sensors 105, where each of the selector elements 111 exhibits thresholding behavior such that for voltages above a given value (i.e., $V_{th}$) the selector element 111 has high conductivity, and below that voltage the conductivity of the selector element 111 is effectively zero. The selector elements 111 may comprise, for example, transistors, diodes, etc. As will be appreciated by those having ordinary skill in the art, different schemes of addressing (selecting) the magnetic sensors 105 (individually or in groups) can be used that ensure only the voltage dropped across the intended magnetic sensor(s) 105 is above $V_{th}$. Accordingly, selector elements 111 may be used reduce the chances of "sneak" currents that could transmit through neighboring elements and degrade the performance of the apparatus 100.

Figure 5E:
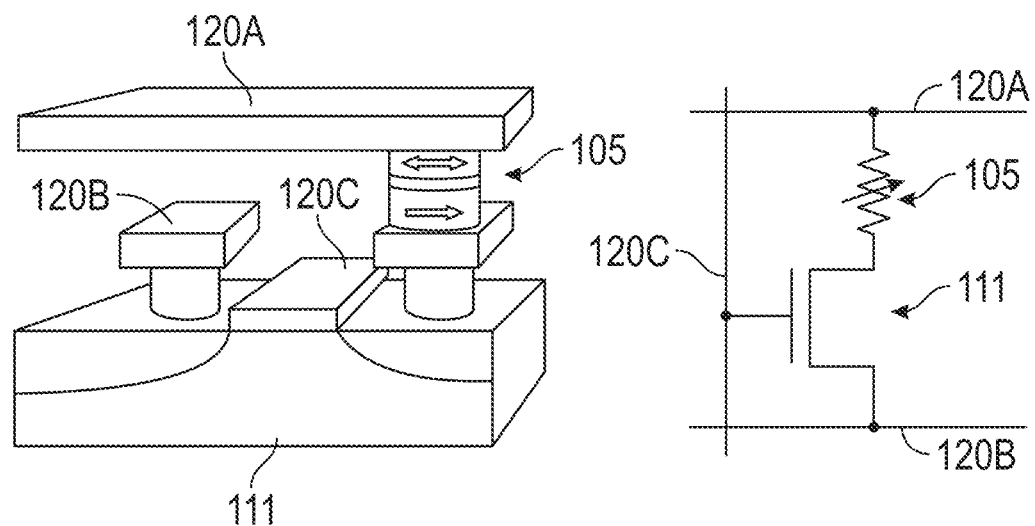
FIG. 5E illustrates a magnetic sensor selection approach in accordance with some embodiments.

FIG. 5E illustrates an exemplary magnetic sensor 105 selection approach in accordance with some embodiments. In the exemplary embodiment shown in FIG. 5E, a respective selector element 111 (e.g., shown as a CMOS transistor) is coupled in series with the magnetic sensor 105. In this exemplary embodiment, three lines 120A, 120B, and 120C allow a characteristic of the magnetic sensor 105 to be sensed. Conceptually, the line 120A may be considered to be a read-out line, the line 120C may be considered to be a control line, and the line 120B may be considered to be either or both a read-out line and a control line. For more detail on configurations such as the exemplary one shown in FIG. 5E, see B. N. Engel, J. Åkerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAM Based on a Novel Bit and Switching Method," IEEE Transactions on Magnetics, Vol. 41, 132 (2005).

Figure 5F:
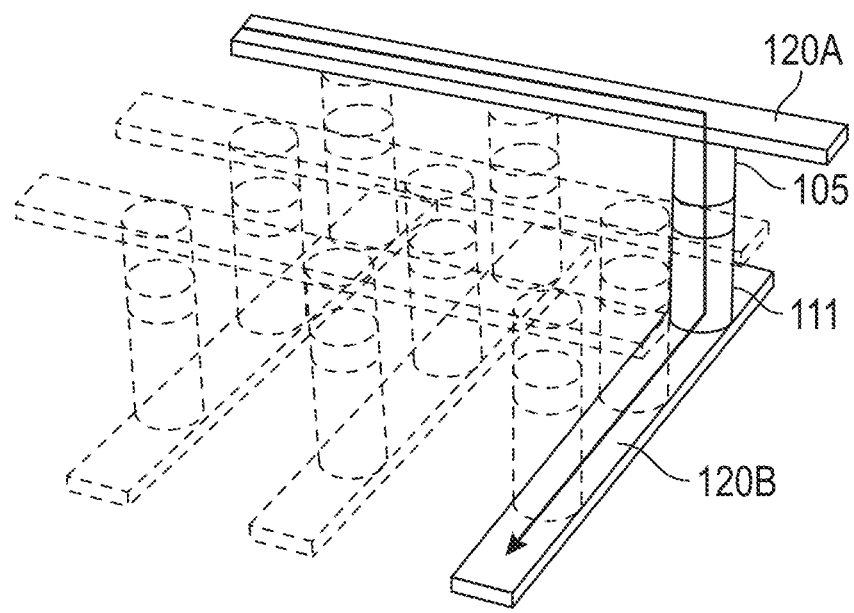
FIG. 5F illustrates another magnetic sensor selection approach in accordance with some embodiments.

FIG. 5F illustrates another exemplary magnetic sensor 105 selection approach in accordance with some embodiments. In the exemplary embodiment shown in FIG. 5F, a selector element 111 (e.g., a diode or a similar thresholding element, as is known in the art, such as semiconductor diodes, operational transconductance amplifiers (OTAs), vanadium oxide layers, capacitive threshold-logic gates, etc.) is deposited "in-stack" together with the magnetic films of the magnetic sensors 105 and then placed into a cross-point architecture. Although FIG. 5F shows the in-stack selector elements 111 over the magnetic sensors 105, it is to be understood that the order of the in-stack selector elements 111 and the magnetic sensors 105 may be reversed. Respective selector devices (e.g., CMOS transistors) may be used to turn on the individual lines 120A, 120B to address/access individual magnetic sensors 105 in the apparatus 100. The use of CMOS select transistors may be simple due to the prevalence of foundries available to fabricate the front end (i.e., all the nanofabrication to build the CMOS transistors and underlying circuitry), but the types of currents used for operation may use a cross-point design to eventually reach the densities desired. Additional details on configurations suitable to select magnetic sensors 105 (e.g., in cross-point arrays) may be found in C. Chappert, A. Fert, and F. N. Van Daul, "The emergence of spin electronics in data storage," Nature Materials, Vol. 6, 813 (2007) and in J. Woo et al., "Selector-less RRAM with non-linearity of device for cross-point array applications," Microelectronic Engineering 109 (2013) 360-363.

Figure 6:
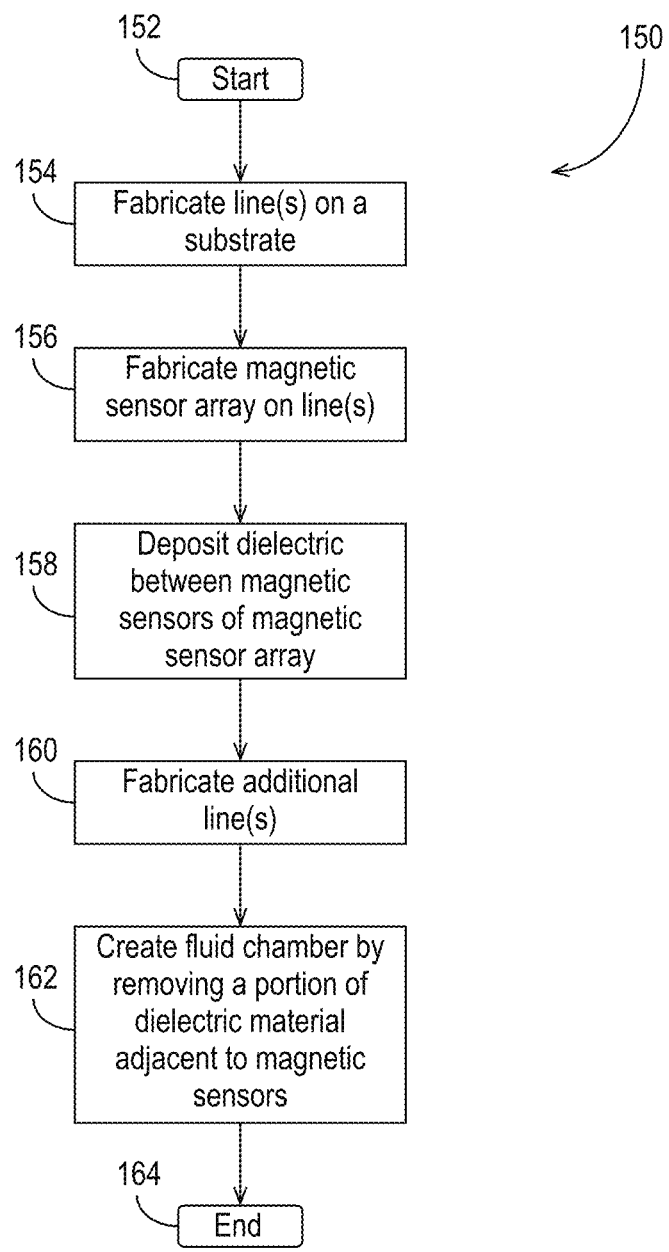
FIG. 6 is a flowchart illustrating a method of manufacturing an apparatus for molecule detection in accordance with some embodiments.
Figure 7:
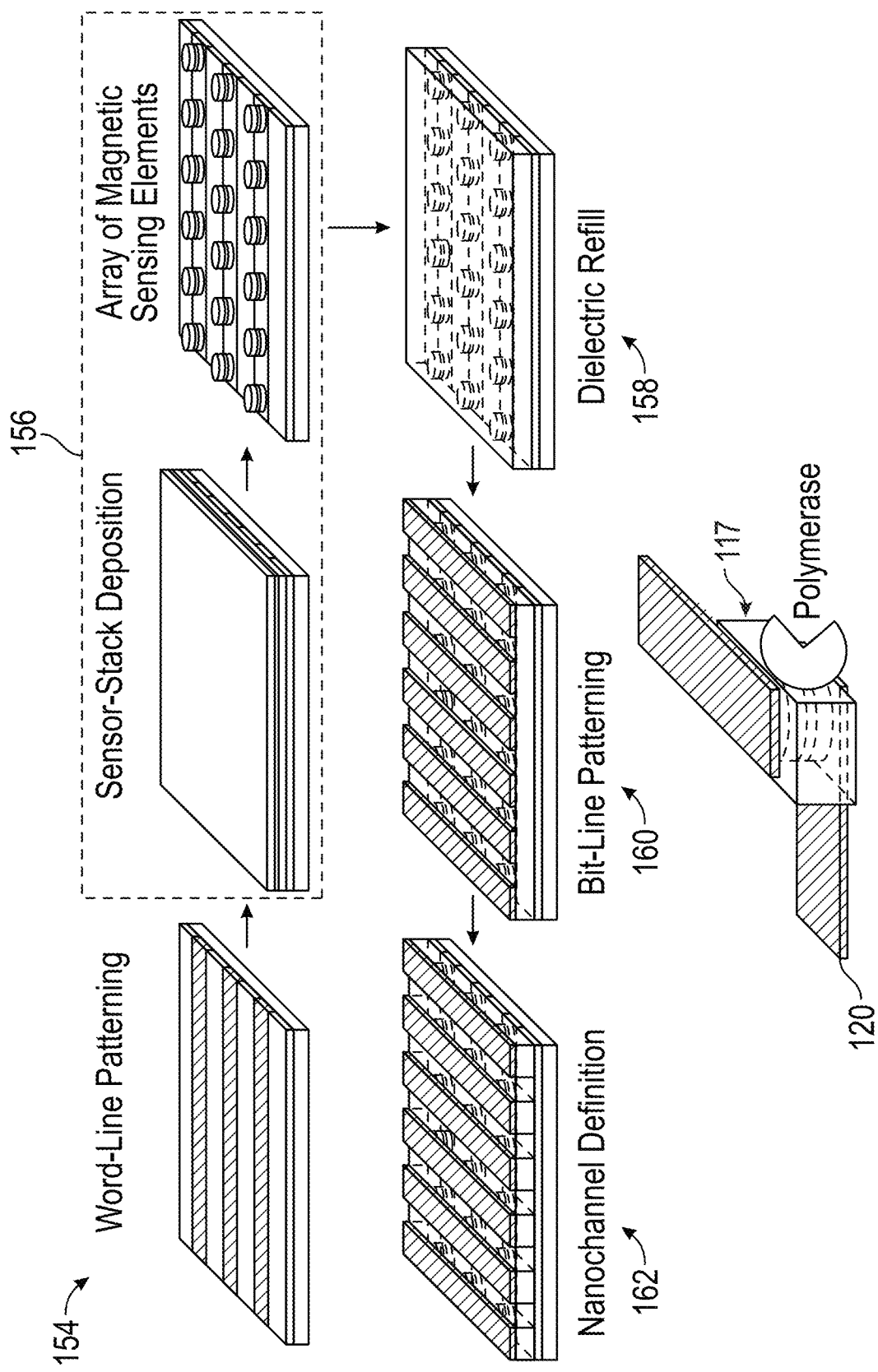
FIG. 7 illustrates the results of each step of the method of manufacturing illustrated in FIG. 6, with a final panel showing a polymerase bound to the edge of a magnetic sensor to be used to capture introduced nucleic acid bases such as DNA bases in accordance with some embodiments.

In some embodiments, the apparatus 100 is fabricated using photolithographic processes and thin film deposition. FIG. 6 illustrates a method 150 of manufacturing the apparatus 100, and FIG. 7 illustrates the results of each step of the fabrication process 150 with a final panel showing polymerase bound to the wall 117 proximate to a magnetic sensor 105 in accordance with some embodiments (e.g., when the apparatus 100 is used for nucleic acid sequencing). At 152, the method begins. At 154, at least one line 120 is fabricated on a substrate, for example, by depositing one or more metal layers, using, for example, photolithography to pattern an array of lines and spaces in a polymer layer applied on top of the metal layers, using that polymer as a mask for etching the metal layers into an array of lines, depositing an insulating dielectric material, stripping the polymer and dielectric over the lines, and performing chemical mechanical polishing to planarize the surface. At 156, the magnetic sensor array 110 is fabricated on the at least one line 120. Each magnetic sensor 105 of the magnetic sensor array 110 has a bottom portion 108 and a top portion 109. (See FIG. 1.) The bottom portion 108 is coupled to the at least one line 120. In some embodiments, the bottom portion 108 of each magnetic sensor 105 is in contact with the at least one line 120.

At 158, dielectric material is deposited between the magnetic sensors 105 of the magnetic sensor array 110. At 160, additional lines 120 are fabricated. Each of these additional lines 120 is coupled to the top portion 109 of at least one magnetic sensor 105 in the magnetic sensor array 110. In some embodiments, the top portion 109 of each magnetic sensor 105 is in contact with an line 120. In some embodiments, the bottom portion 108 of a magnetic sensor 105 is in contact with a first line 120A, and the top portion 109 of the magnetic sensor 105 is in contact with a second line 120B. At 162, a portion of the dielectric material adjacent to the magnetic sensors 105 is removed (e.g., by milling, etching, or any other suitable removal process) to create the fluidic channel 115. At 164, the process 150 ends.

As described herein, the exemplary apparatus 100 shown in FIG. 7 can be used with methods using SBS protocols that use magnetically-labeled nucleotide precursors. SBS involves binding of primer-hybridized template DNA, incorporation of a deoxynucleoside triphosphate (dNTP), and detection of incorporated dNTP. The apparatus 100 (as shown in FIGS. 4A-4C and FIGS. 5A-5E) can be used to expose the magnetic sensors 105 to sequencing reagents in the fluidic channel(s) 115 while protecting the magnetic sensors 105 using, for example, an electrically-insulating material. DNA synthesis may be performed using polymerase molecules placed in the proximity of the magnetic sensors 105, which detect MNPs (e.g., as shown in the final panel of FIG. 7).

In particular, either molecules of polymerase or fragments of single-strand nucleic acid may be attached to the side wall(s) 117 of the fluidic channel(s) 115 in the proximity of one or more of the magnetic sensors 105. Sequencing can then be performed by adding, to the fluidic channel(s) 115, a nucleic acid template (having a primer binding site and an extendable primer) and magnetically-labeled nucleotide precursors (each type of nucleotide precursor labeled by a distinguishable MNP), and sequencing the nucleic acid template by using the lines 120 to detect a characteristic of the magnetic sensors 105 that indicates which of the magnetically-labeled nucleotide precursors has been incorporated into the extendable primer. For DNA sequencing specifically, because adenine (A) pairs only with thymine (T) and cytosine (C) pairs only with guanine (G), detection of the MNPs enables the determination of which of the magnetically-labeled nucleotide precursors has been incorporated. Specifically, if the MNP labeling A is detected, the recorded base is T (and vice versa), and if the MNP labeling C is detected, the recorded base is G (and vice versa).

Some methods of using embodiments of the apparatus 100 described above rely on the use of molecules that are magnetically-labeled by magnetic nanoparticles, such as, for example, a magnetic molecule, a superparamagnetic nanoparticle, or a ferromagnetic particle. These magnetic nanoparticles may be cleavable. For example, for nucleic-acid sequencing applications, nucleotide precursors to be sequenced may comprise cleavable MNPs.

There are a number of ways to attach and (if applicable) cleave the MNPs. For example, the MNPs may be attached to a base or a molecule to be detected, in which case they may be cleaved chemically. As another example, the MNPs may be attached to a phosphate, in which case they may be cleaved by, for example, polymerase or, if attached via a linker, by cleaving the linker.

In some embodiments for nucleic acid sequencing, the magnetic label is linked to the nitrogenous base (A, C, T, G, or a derivative) of the nucleotide precursor. After incorporation of the nucleotide precursor and the detection by the apparatus 100 (i.e., using the magnetic sensor array 110), the magnetic label may be cleaved from the incorporated nucleotide.

In some embodiments, the magnetic label is attached via a cleavable linker. Cleavable linkers are known in the art and have been described, e.g., in U.S. Pat. Nos. 7,057,026, 7,414,116 and continuations and improvements thereof. In some embodiments, the magnetic label is attached to the 5-position in pyrimidines or the 7-position in purines via a linker comprising an allyl or azido group. In other embodiments, the linker comprises a disulfide, indole and/or a Sieber group. The linker may further contain one or more substituents selected from alkyl ($C_{1-6}$) or alkoxy ($C_{1-6}$), nitro, cyano, fluoro groups or groups with similar properties. Briefly, the linker can be cleaved by water-soluble phosphines or phosphine-based transition metal-containing catalysts. Other linkers and linker cleavage mechanisms are known in the art. For example, linkers comprising trityl groups, p-alkoxybenzyl ester groups, p-alkoxybenzyl amide groups, tert-butyloxycarbonyl (Boc) groups. and the acetal-based groups can be cleaved under acidic conditions by a proton-releasing cleavage agent such as an acid. A thioacetal or other sulfur-containing linker can be cleaved using a thiophilic metals, such as nickel, silver or mercury. The cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising o-nitrobenzyl groups. Linkers comprising benzyloxycarbonyl groups can be cleaved by Pd-based catalysts.

In some embodiments, the nucleotide precursor comprises a label attached to a polyphosphate moiety as described in, e.g., U.S. Pat. Nos. 7,405,281 and 8,058,031. Briefly, the nucleotide precursor comprises a nucleoside moiety and a chain of 3 or more phosphate groups where one or more of the oxygen atoms are optionally substituted, e.g., with S. The label may be attached to the $\alpha$, $\beta$, $\gamma$ or higher phosphate group (if present) directly or via a linker. In some embodiments, the label is attached to a phosphate group via a non-covalent linker as described, e.g., in U.S. Pat. No. 8,252,910. In some embodiments, the linker is a hydrocarbon selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl; see, e.g., U.S. Pat. No. 8,367,813. The linker may also comprise a nucleic acid strand; see, e.g., U.S. Pat. No. 9,464,107.

In embodiments in which the magnetic label is linked to a phosphate group, the nucleotide precursor is incorporated into the nascent chain by the nucleic acid polymerase, which also cleaves and releases the detectable magnetic label. In some embodiments, the magnetic label is removed by cleaving the linker, e.g., as described in U.S. Pat. No. 9,587,275.

In some embodiments, the nucleotide precursors are non-extendable "terminator" nucleotides, i.e., the nucleotides that have a 3'-end blocked from addition of the next nucleotide by a blocking "terminator" group. The blocking groups are reversible terminators that can be removed in order to continue the strand synthesis process as described herein. Attaching removable blocking groups to nucleotide precursors is known in the art. See, e.g., U.S. Pat. Nos. 7,541,444, 8,071,739 and continuations and improvements thereof. Briefly, the blocking group may comprise an allyl group that can be cleaved by reacting in aqueous solution with a metal-allyl complex in the presence of phosphine or nitrogen-phosphine ligands.

FIGS. 8A through 8C illustrate an embodiment of a cross-point array architecture 300 that may be included in the apparatus 100 in accordance with some embodiments. For illustration, the magnetic sensors 105 illustrated in FIGS. 8A through 8C comprise MTJ elements 308, but it is to be appreciated that other types of sensors (e.g., spin valve devices) may be used. It is to be appreciated that although various particular MR sensor types were described above, the description is not intended to exclude other MR sensor types.

Referring to FIG. 8A, the cross-point array architecture 300 includes top wires 318 and bottom wires 320 (each of which is an line 120). As shown in the exemplary embodiment of FIG. 8A, the top wires 318 are oriented at substantially 90° angles to the bottom wires 320 as shown. An example MTJ element 308 is situated between a crossing of the array. The example MTJ element 308 includes two or more FM layers separated by one or more non-magnetic layers 316 (e.g., MgO). As shown, one of the FM layers is a free layer 310 that will rotate in the presence of a magnetic field, and another of the FM layers is a pinned (or fixed) layer 314 that may be a single FM coupled to an AFM layer 312. Alternatively, a compound structure called a synthetic antiferromagnet (SAF) may be used. The SAF includes two FM layers separated by a magnetic coupling layer (e.g., ruthenium), with one of the two FM layers coupled to an AFM layer. It is to be understood that although the example layer arrangement of MTJ element 308 shows a general structure with layers over or under other layers, intervening layers not shown can be inserted.

To illustrate some of the features of the cross-point array architecture 300, FIG. 8B shows a cross-section of the cross-point array architecture 300 along the top wire 318 direction (indicated in FIG. 8A by the dash-dot line labeled "8B"), and FIG. 8C shows a cross-section of the cross-point array architecture 300 along the bottom wire 320 direction (indicated in FIG. 8A by the dashed line labeled "8C"). As shown, the sides of the MTJ elements 308 (which may be the magnetic sensors 105) are encapsulated by insulating material 336. Optionally, as shown in FIG. 8B, a hard bias magnetic material 338 may also be deposited between the MTJ elements 308. If present, the hard bias magnetic material 338 may be magnetized to point in a direction parallel to the direction of the top wire(s) 318. In embodiments including hard bias magnetic material 338, a thin layer of insulator 340 is also deposited on top of the hard bias magnetic material 338 to electrically insulate it from the top wire(s) 318.

In some embodiments, the orientation of the free layer 310 moment is at an angle approximately 90° from the pinned layer 314 moment (as shown in the left side panel of FIG. 9A, discussed further below), which can be achieved using one or more strategies. The first is by using a hard bias field in which the hard bias magnetized along the direction of the top magnet also applies a magnetic field across the MTJ elements 308 in the direction of the top wire 318. Because the pinned layer 314 is fixed using an AFM layer 312, its moment can be chosen to be perpendicular to the hard bias field, but the free layer 310 will rotate to be roughly parallel to the hard bias field.

A second way to achieve this orientation configuration is to pattern the MTJ elements 308 into rectangles or ellipses, where the long axis of the MTJ elements 308 is along the direction of the top wire(s) 318. Through the aspect ratio of these shapes, a shape anisotropy energy can be tuned, which creates an axis along the length of the top wire(s) 318 along which the free layer 310 magnetization will preferentially point in the absence of an external magnetic field.

A third way to achieve this orientation configuration is by etching the FM layers 310, 314 along an axis to induce texturing (see, e.g., U.S. Pat. No. 7,382,586), which can also create uniaxial anisotropy so that the free layer 310 moment will point along the length of the top wire(s) 318.

A fourth way to achieve this orientation configuration is to use perpendicular magnetic anisotropy to pull the free layer 310 out of plane while keeping the pinned layer 314 in the plane of the film, or vice versa. The anisotropy of the free layer 310 is kept small enough that a small in-plane field can rotate the free layer 310 in plane, which is qualitatively similar to the other methods described above. There are other methods to achieve a 90° orientation between the free and pinned layer moments in addition to those mentioned here, and achieving this orientation is not limited to these options.

Referring to FIG. 8C, the cross section shows the fluidic channels 115 (e.g., nanofluidic or microfluidic channels), which may be, for example, trenches etched in an insulator. As shown, a small amount of insulator 322 is left on the sidewalls of the magnetic sensors 105 (illustrated as MTJ elements 308) so that the MNPs do not electrically interact with the magnetic sensors 105. The portion of the insulator exposed to (and forming) the fluidic channel 115 may form the wall 117 to which polymerase molecules or molecules to be detected (e.g., nucleic acid samples) may be attached for sequencing.

Detection of MNPs can be performed in a variety of ways. To achieve high-throughput sequencing relying on each magnetic sensor 105 being capable of detecting a single MNP (e.g., a nanoparticle), the MNPs should be small, ideally comparable to the size of an individual magnetic sensor 105. This can be achieved with a variety of MNPs that can be readily synthesized as is known in the art. For example, the MNPs may be nanoparticles with high magnetic anisotropy. Examples of nanoparticles with high magnetic anisotropy include, but are not limited to, $Fe_3O_4$, FePt, FePd, and CoPt. To facilitate chemical binding to nucleotides, the particles may be synthesized and coated with $SiO_2$. See, e.g., M. Aslam, L. Fu, S. Li, and V. P. Dravid, "Silica encapsulation and magnetic properties of FePt nanoparticles," Journal of Colloid and Interface Science, Volume 290, Issue 2, 15 Oct. 2005, pp. 444-449.

Because MNPs of this size have permanent magnetic moments, the directions of which fluctuate randomly on very short time scales, some embodiments rely on sensitive sensing schemes that detect fluctuations in magnetic field caused by the presence of the MNPs.

In some embodiments, the sensing circuitry 130 detects deviations or fluctuations in the magnetic environment of some or all of the magnetic sensors 105 in the magnetic sensor array 110. For example, a magnetic sensor 105 of the MR type in the absence of a MNP should have relatively small noise above a certain frequency as compared to a magnetic sensor 105 in the presence of a MNP, because the field fluctuations from the MNP will cause fluctuations of the moment of the sensing ferromagnet. These fluctuations can be measured using heterodyne detection (e.g., by measuring noise power density) or by directly measuring the voltage of the magnetic sensor 105 and evaluated using a comparator circuit to compare to a dummy sensor element that does not sense the fluidic channel 115. One advantage of the array design embodiment illustrated in FIG. 2A is that multiple magnetic sensors 105 (e.g., nominally to the left and right of a MNP) can be used in post-processing of data to improve the accuracy of MNP detection.

In applications in which the apparatus 100 is used to detect biologic molecules (e.g., for nucleic acid sequencing applications), it may be difficult to orient the moments of each of the MNPs (e.g., nanoparticles) in the same direction, as the position of each label with respect to a magnetic sensor 105 as well as the axis of the label's magnetic moment can vary. Moreover, to achieve high densities of magnetic sensors 105 in the magnetic sensor array 110, the MNPs may need to be on the order of tens of nanometers, in which case the MNPs are likely to be superparamagnetic, meaning that they maintain a measurable moment without a defined axis for the moment to point (i.e., the magnetic field acting on a magnetic sensor 105 would fluctuate in time in its direction). These challenges can increase the difficulty of accurate detection. To mitigate these challenges, an external magnetic field may be used (e.g., to align the moments of the MNPs in substantially the same direction) as well as to address the magnetic sensors 105.

Figure 9A:
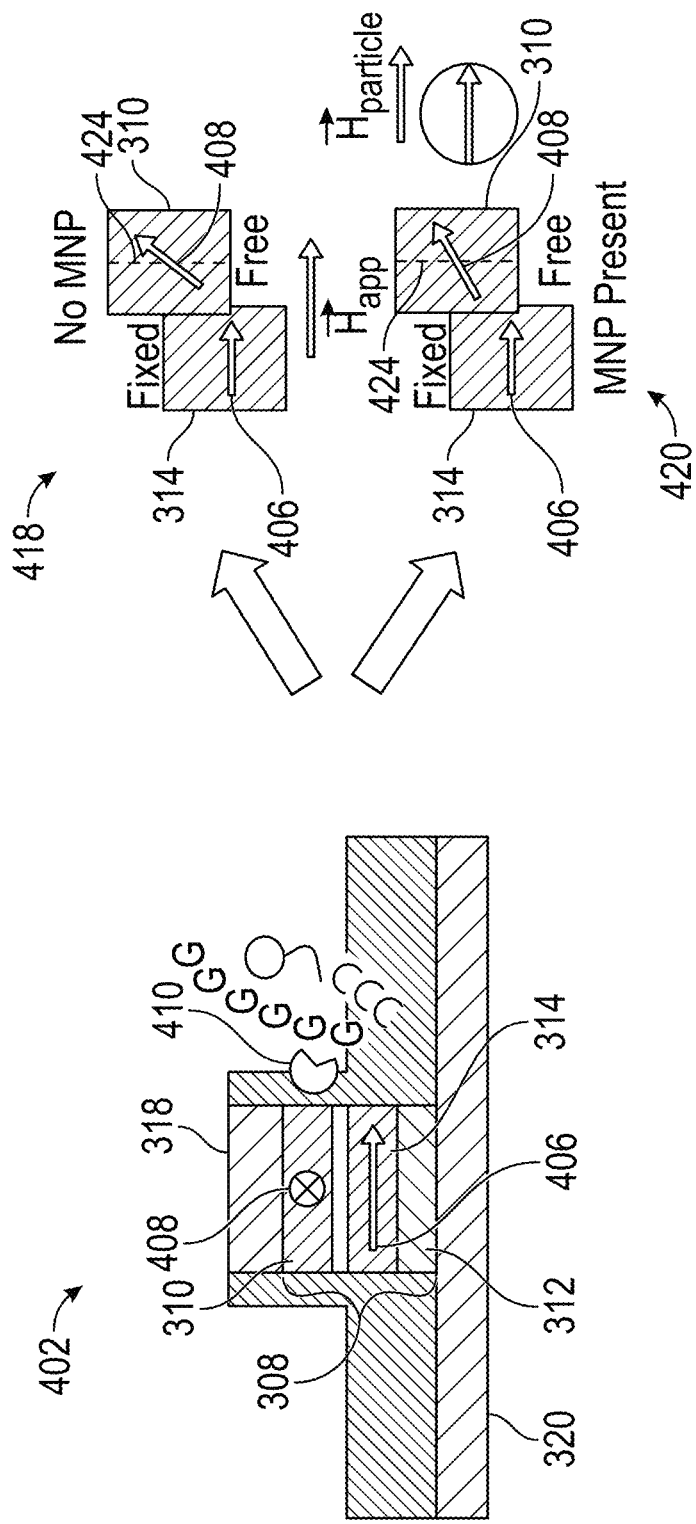
FIGS. 9A and 9B illustrate a magnetic sensor and detection using that magnetic sensor in accordance with some embodiments.

In some embodiments, target molecules to be detected (e.g., nucleic acid strands to be sequenced) are attached to the walls 117 of the fluidic channels 115 as shown in the left panel of FIG. 9A and may have polymerase introduced at this point. Individual bases with attached MNPs may then be introduced into the fluidic channels 115. The appropriate (complementary) base pair (i.e., for DNA sequencing, cytosine (C) with guanine (G) or adenine (A) with thymine (T)) will then be incorporated and can be detected. Assuming this process is done one base pair at a time, sub-panel 402 (left) of FIG. 9A illustrates a detection method according to an embodiment in which the presence or absence of the MNP, and therefore the base, can be determined using the various device embodiments of, for example, FIGS. 4A-4C, 5A-5D, and 8A-8C. As shown in sub-panel 402, polymerase 410 is bound to the wall 117 and is used to capture induced DNA bases for detection. The MNPs used can be either superparamagnetic or weakly magnetic, as it is beneficial that they do not require a large magnetic field to align their moments to the magnetic field.

Sequencing occurs by applying a magnetic field (Happ) across the MTJ element 308 (an example of the magnetic sensor 105). The magnetic field may be applied using an electromagnet, e.g., by placing the pole pieces on either side of the apparatus 100), a distributed coil, a solenoid oriented perpendicular to the fluidic channel 115, etc. to generate the magnetic field in the direction of the pinned layer's moment 406. The means for generating the magnetic field may be mounted, for example, on the bottom surface 119 of the apparatus 100. As another example, the means for generating a magnetic field may be included in a system that includes the apparatus 100. It is to be understood that other suitable means of generating the magnetic field, such as, for example, by using permanent magnets or super-conducting magnets, are possible, are specifically contemplated herein, and are not excluded.

The applied magnetic field can achieve at least two objectives: (1) it aligns the moments of all the MNPs in a common direction so that the measured signals due to the presence of a MNP are similar, and (2) it rotates the free layer's moment 408 toward (or away from, depending on the field orientation) the pinned layer's moment 406 and thus changes the resistance of the magnetic sensor 105 from its equilibrium resistance.

The right-hand portion of FIG. 9A illustrates the pinned layer 314 (labeled "fixed") and free layer 310 as if viewing sub-panel 402 from above. The pinned layer 314 and free layer 310 are drawn offset from each other to illustrate their moments. The dashed line 424 shown in the free layer 310 is the equilibrium direction of the free layer 310's moment. In the absence of a MNP near the MTJ element 308 (or, more generally, the magnetic sensor 105), illustrated as case 418 (top) on the right-hand side of FIG. 9A, the magnetic field can rotate the magnetic moment 408 of the free layer 310 into the direction of the magnetic moment 406 of the pinned layer 314 (depending on the details of the MTJ element 308/magnetic sensor 105 design). In the presence of a MNP near the MTJ element 308 (or, more generally, the magnetic sensor 105), illustrated as case 420 (bottom) on the right-hand side of FIG. 9A, fringing fields (Hparticle) will be created. These fringing fields will be in the same direction as the applied field and, therefore, can add significantly to the applied field locally near the magnetic sensor 105 (shown as a MTJ element 308). The magnetic moment 408 of the free layer 310 will then rotate more substantially from its equilibrium position (dashed line 424), as shown in case 420. Therefore, by connecting the magnetic sensors 105 to detection electronics that measure the resistance of the magnetic sensors 105 (or a proxy for the resistance, such as, for example, the voltage across the magnetic sensors 105 for a given current), the presence or absence of a MNP can be detected. The detection can be accomplished by either measuring the absolute resistance of each magnetic sensor 105 (e.g., each MTJ element 308) or by comparing the resistances to a reference cell or bit (e.g., a magnetic sensor 105 that is completely encapsulated such that it is not exposed to or affected by the field from a MNP).

Figure 9B:
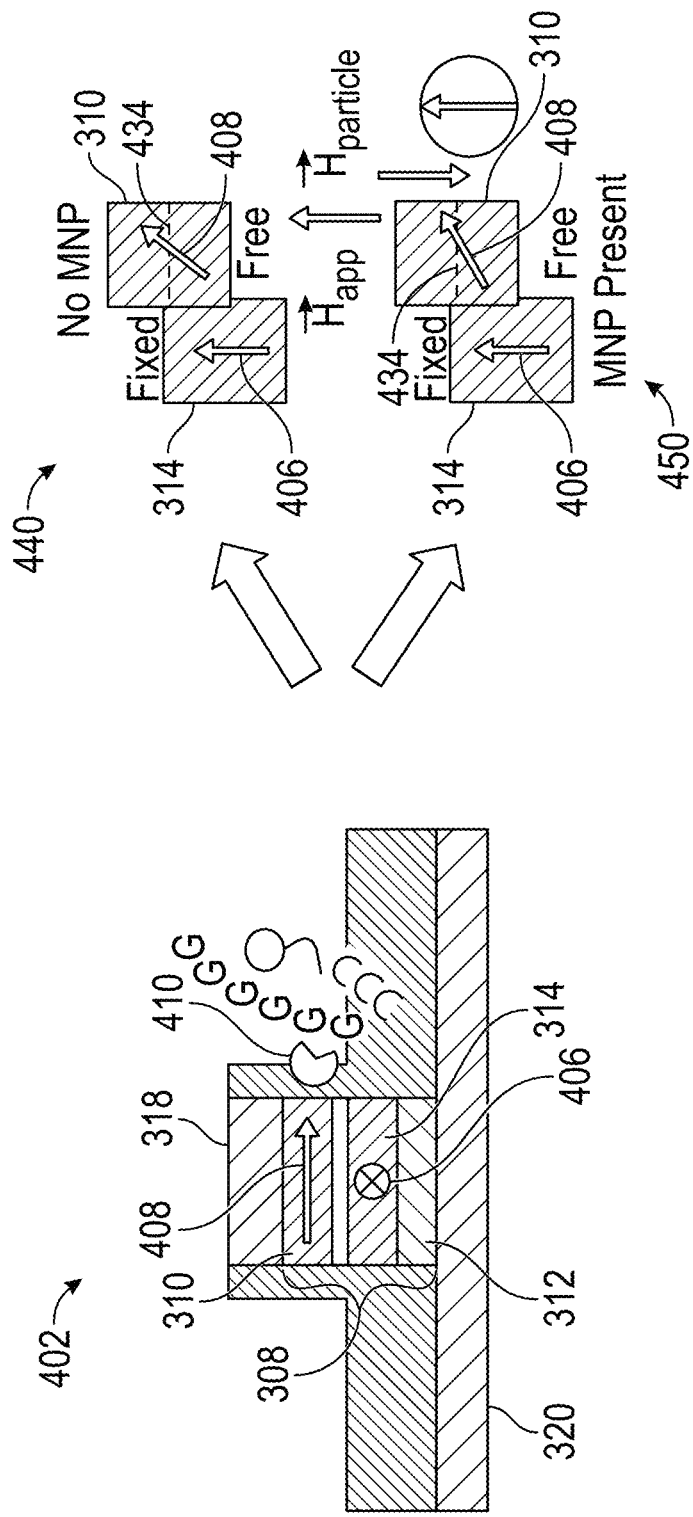

FIG. 9B illustrates another embodiment in which the magnetic moments 408 and 406 of, respectively, the free layer 310 and pinned layer 314 are reversed in arrangement relative to FIG. 9A. The dashed line 434 shown in the free layer 310 is the equilibrium direction of the free layer 310's moment. As FIG. 9B illustrates, if the applied field Happ is in the direction along the fluidic channel 115, the fringing field Hparticle will be in an opposite direction to the applied field Happ. Thus, in the absence of a MNP near the MTJ element 308 (or, more generally, the magnetic sensor 105), illustrated as case 440 (top) on the right-hand side of FIG. 9B, the magnetic field can rotate the magnetic moment 408 of the free layer 310 into the direction of the magnetic moment 406 of the pinned layer 314 (depending on the details of the MTJ element 308/magnetic sensor 105 design). In the presence of a MNP, however, the magnetic moments 408 and 406 will be closer to a 90-degree alignment as shown in the bottom portion of the right-hand side of FIG. 9B (case 450).

Using the detection methodology described above for DNA sequencing, for example, detecting which of four magnetically-labeled nucleotide precursors has been incorporated into the extendable primer can be accomplished in four chemistry steps, one for each of the four bases. In each step, a binary (yes/no, 1/0, etc.) determination may be made as to whether the magnetically-labeled nucleotide precursor being tested has been incorporated.

In another embodiment, instead of using a binary method with four chemistry steps for each read, either three or four different MNPs can be used as the magnetic labels. Each of the different MNPs has a different saturation magnetization so that it generates a magnetic field of a magnitude that distinguishes it from the magnetic fields generated by all other MNPs being used as magnetic labels. For example, in a DNA sequencing application, A can be labeled using MNP1, T using MNP2, C using MNP3, and G either using MNP4 or left unlabeled, where the saturation magnetizations of MNP1, MNP2, MNP3, and (if used) MNP4 are all different enough that the three or four types of particles can be distinguished. Then all four bases can be introduced into the fluidic channel 115 at the same time, and the magnitude of the resistance detected via the magnetic sensors 105 can be used to identify which MNP (and therefore base) is incorporated in the vicinity of each magnetic sensor 105. For example, assume the resistance of a magnetic sensor 105 is expected to vary in accordance with the following table in the presence of four different MNPs:

| Magnetic nanoparticle identity | Expected minimum resistance | Expected maximum resistance | Base labeled |
| --- | --- | --- | --- |
| MNP1 | R1 | <R2 | A |
| MNP2 | R2 | <R3 | T |
| MNP3 | R3 | <R4 | C |
| MNP4 | R4 | <R5 | G |

In some embodiments, the expected resistance ranges are nonoverlapping. Thus, assume that R1<R2<R3<R4<R5. If the detected resistance of a magnetic sensor 105 is greater than R2 but less then R3, it can be determined that thymine (T) was incorporated, and that the base of the DNA strand being sequenced is adenine (A).

It is to be understood that it is not necessary to use four MNPs. In some embodiments, one of the bases is unlabeled. Using the example above, and assuming that guanine (G) is left unlabeled, the table becomes:

| Magnetic nanoparticle identity | Expected minimum resistance | Expected maximum resistance | Base labeled |
| --- | --- | --- | --- |
| MNP1 | R1 | <R2 | A |
| MNP2 | R2 | <R3 | T |

-continued

| Magnetic nanoparticle identity | Expected minimum resistance | Expected maximum resistance | Base labeled |
|---|---|---|---|
| MNP3 | R3 | <R4 | C |
| MNP4 | Reference (optionally minus tolerance) | Reference (optionally plus tolerance) | G |

Relative to the example above, the incorporation of A, T, and C is done as previously described, but the incorporation of G is detected by detecting that the resistance of a magnetic sensor 105 is approximately a reference value (i.e., whatever the expected value of the resistance is in the absence of any MNP). Optionally, a tolerance can be used to create the detection range for the unlabeled base to account for variations in the expected resistance of a magnetic sensor 105 that is not in the presence of any MNP.

After some or all sensors have been addressed and read, the magnetic field can be turned off and the MNPs may be cleaved from the incorporated magnetically-labeled nucleotide precursor using, for example, enzymatic or chemical cleavage, as is known in the art. The process can then be repeated for the next unpaired base in the strand being sequenced. This embodiment allows for a single chemistry step per base read.

In some embodiments, instead of applying an external magnetic field and detecting the resistances (or a proxy for resistance, such as voltage at a particular current) of the magnetic sensors 105 to detect the presence or absence of a MNP, the magnetic noise of the magnetic sensors 105 is detected (e.g., estimated, measured, etc.) without applying an external magnetic field. Specifically, as described below, fluctuations in the magnetic noise may be detected and used to determine whether a MNP is present.

A magnetic sensor 105 has an intrinsic magnetic noise because the magnetic moments of the materials in the magnetic sensor 105 fluctuate about their equilibrium positions. Magnetic noise occurs due to thermal noise that causes the moment of a ferromagnet to undergo small fluctuations in direction over short time periods. This fluctuation translates to measurable noise signals in a MR device, because these effects cause fluctuations in the device resistance (or measured voltage for a given current). In the frequency domain, these fluctuations are called 1/f (where f is frequency) noise because the magnitude of the noise is proportional to 1/f. The characteristics (e.g., variance, amplitude, etc.) of the intrinsic magnetic noise can be determined in the absence of any magnetic particle near the magnetic sensor 105. Changes to the characteristics of the magnetic noise can indicate the presence of a MNP near the magnetic sensor 105.

Referring again to FIGS. 8A-8C, when the MNPs used to label the magnetically-labeled nucleotide precursors are superparamagnetic, the noise of a particular magnetic sensor 105 (illustrated as MTJ element 308) will change when a MNP is nearby because the magnetic sensor 105 will also be exposed to a locally-fluctuating magnetic field due to the MNP, which can change both the amplitude and the frequency response of the magnetic sensor 105's noise. By monitoring/detecting the amplitude of the noise (e.g., at specific frequencies or over a frequency band), or another characteristic of the noise, such as its fluctuations, or changes in the amplitude and/or another characteristic of the noise of a particular magnetic sensor 105, the presence or absence of a MNP in the vicinity of that particular magnetic sensor 105 can be detected.

Figure 10A:
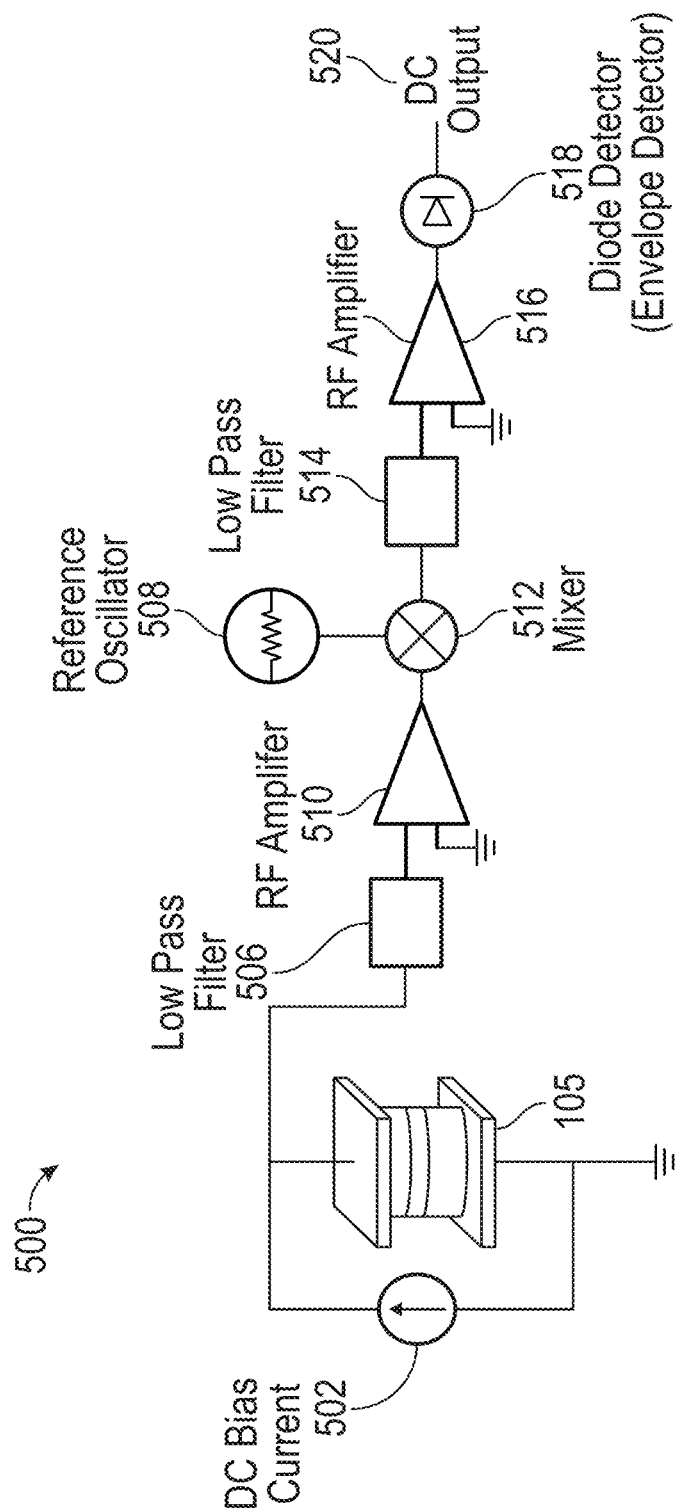
FIG. 10A is a detection circuit in accordance with some embodiments.

Particle detection can be accomplished in several different ways. As one example, the noise amplitude (e.g., at one or more frequencies or within one or more frequency bands) can be measured using a super-heterodyne circuit 500, such as the exemplary embodiment shown in FIG. 10A. As shown in FIG. 10A, a (typically small) bias current 502 (e.g., a DC bias current) is applied to a magnetic sensor 105 (which may be, for example, a MTJ element 308 or any other suitable magnetic sensor 105), and the resultant signal is filtered by a low pass filter 506 having a suitable cutoff frequency (e.g., a cutoff frequency below 100 MHz). The signal is then amplified by an amplifier 510 (e.g., a RF amplifier), and a mixer 512 multiplies the signal by a reference signal from a local reference oscillator 508. The local reference oscillator 508 has a fixed frequency chosen to maximize the change in signal at that frequency when a particular MNP is present. The frequency of the local reference oscillator 508 may be different to detect different MNPs. The output of the mixer 512 is filtered by a second low pass filter 514 (which may be similar or identical to the low pass filter 506) and amplified by a second amplifier 516 (e.g., a RF amplifier). The signal is sent through an envelope detector, shown in FIG. 10A as a diode detector 518. The output 520 of the envelope detector (diode detector 518) is then sent to detection electronics that measure the voltage of the signal. This voltage is proportional to the noise of the magnetic sensor 105. Therefore, changes in the noise level (e.g., an increase or decrease in the voltage level (noise amplitude)) over time can indicate the presence or absence of a MNP.

Figure 10B:
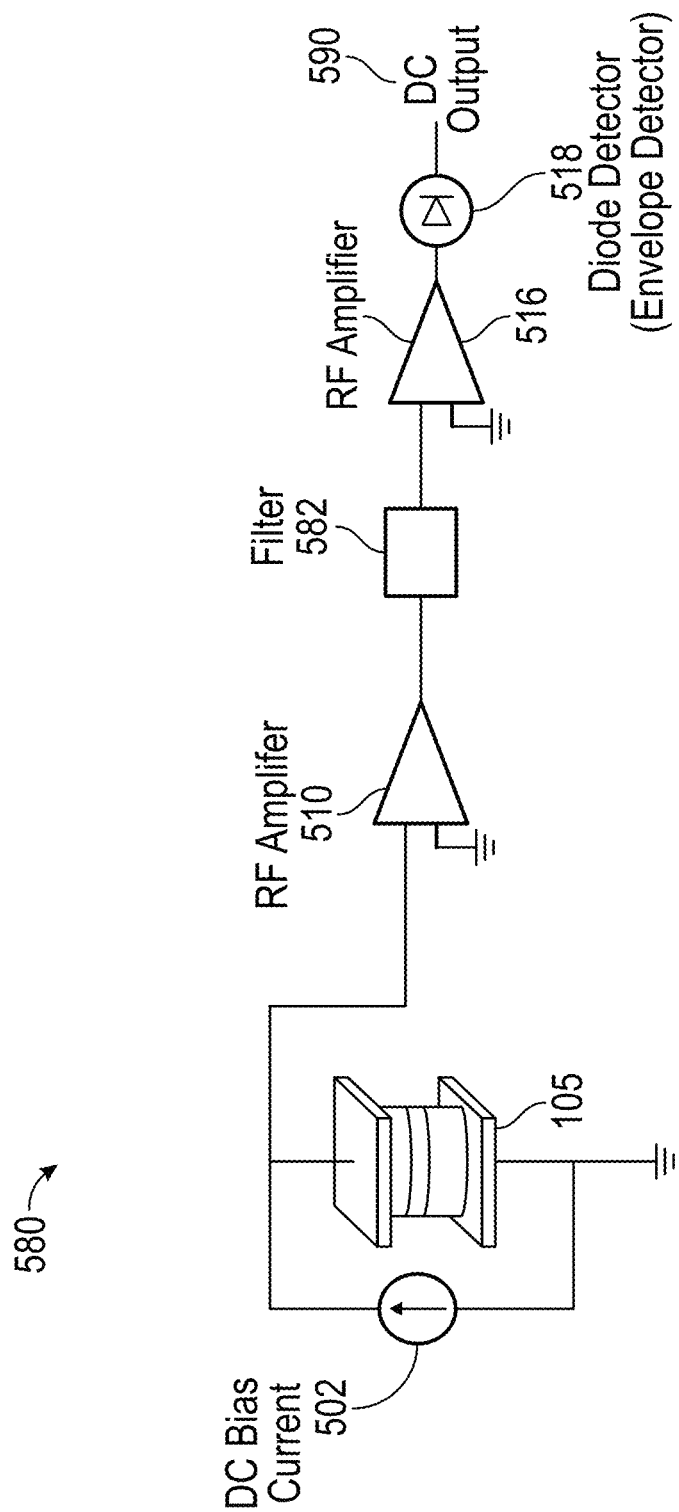
FIG. 10B is another detection circuit in accordance with some embodiments.

An alternative detection circuit 580, which enables detection of fluctuations in the magnetic noise (sometimes referred to as "mag noise"), is illustrated in FIG. 10B. As shown in FIG. 10B, a bias current 502 (e.g., a DC bias current) is applied to a magnetic sensor 105 (which may be, for example, a MTJ element 308 or any other suitable magnetic sensor 105), and the resultant signal is amplified by a RF amplifier 510 and filtered by a filter 582 (e.g., a bandpass filter) having a suitable cutoff frequency selected to allow the mag noise jitter in the presence of a MNP to be distinguished from the mag noise jitter in the absence of a MNP (e.g., a band of frequencies of approximately 1 kHz to 100 MHz). The signal may then (optionally) be amplified by another amplifier 516 (e.g., a RF amplifier), and an envelope detector, shown in FIG. 10B as a diode detector 518, provides a DC output 590. The DC output 590 is nonzero when a MNP is present because the fluctuations in the mag noise will be higher in the presence of a MNP than in the absence of a MNP. Therefore, changes in the DC output 590 over time can indicate the presence or absence of a MNP.

Figure 11:
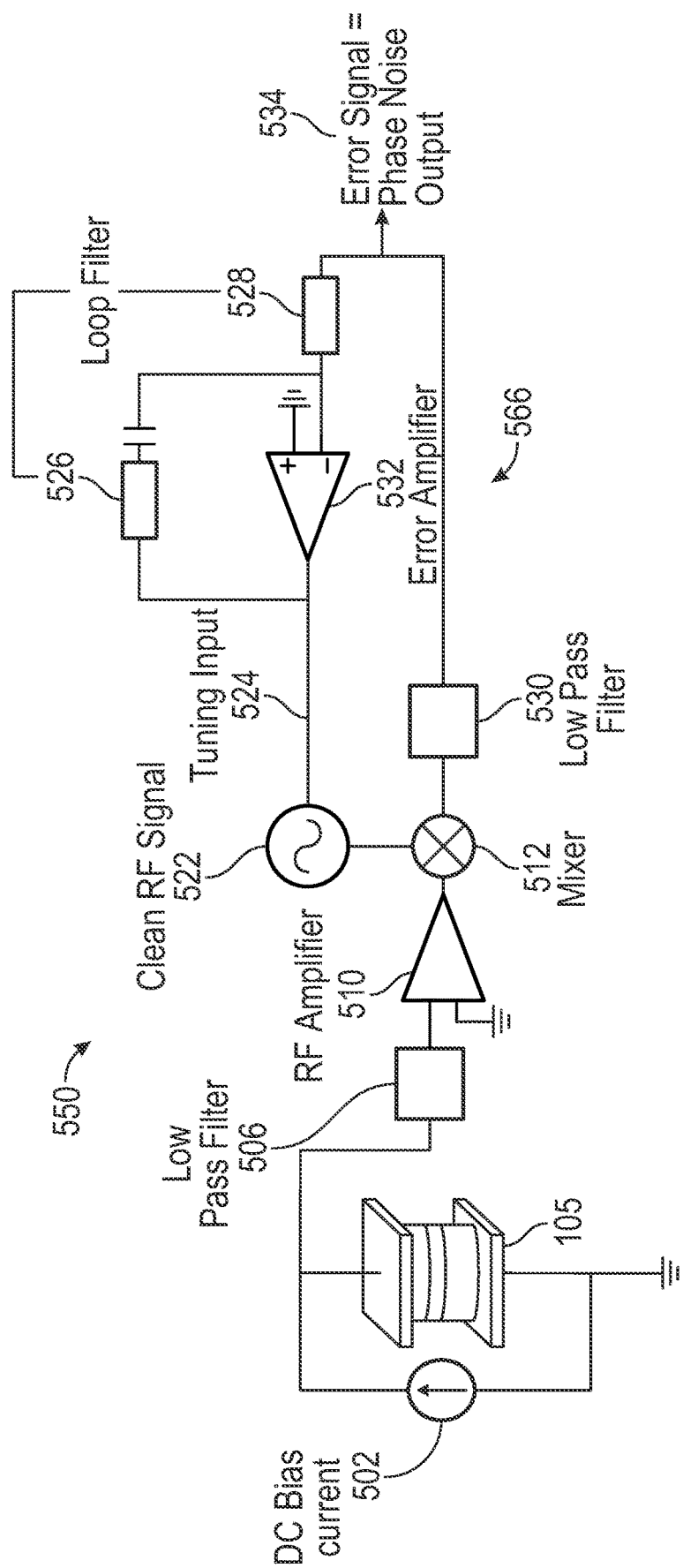
FIG. 11 is another detection circuit in accordance with some embodiments.

An alternative embodiment of a detection circuit 550 is shown in FIG. 11. The circuit 550 allows the mag noise of the magnetic sensor 105 to be measured directly. In the detection circuit 550, the AC response of the magnetic sensor 105's mag noise is tracked by a phase locked loop (PLL) 566. The circuit 550 includes many of the same elements as the detection circuits 500 and 580 shown in FIGS. 10A and 10B, and the descriptions of those elements are not repeated here.

In the exemplary embodiment of FIG. 11, the PLL 566 includes a signal generator 522, which generates a clean RF signal based on a tuning input 524. The tuning input 524 comes from components 526 and 528 forming a loop filter with an error amplifier 532. The clean RF signal from the signal generator 522 is combined (mixed) with the signal coming from the amplifier 510 at a mixer 512, and then filtered by a low pass filter 530 of the PLL 566. The resultant error signal 534 of the PLL 566 is the magnetic noise of the magnetic sensor 105, the characteristics of which depend on (e.g., are influenced or changed by) the presence or absence of a MNP. Thus, the error signal 534 can be used to detect the presence or absence of a MNP.

Electrical detection for DNA sequencing as described in this disclosure has several advantages over currently used technologies involving optical detection methods, with a primary advantage being that electrical detection is not limited in terms of scaling flow cell dimensions in the same manner that optical detection is limited due to optical imaging being diffraction limited. Magnetic detection is a form of electrical detection for sequencing that has advantages over commonly proposed tunnel current detection schemes, because tunneling current methods rely on the measurement of extremely small currents (which reduces SNR), and the tunnel junction elements to be exposed directly to the sequencing chemistries, which could cause corrosion or other detrimental issues that degrade the accuracy of the sequencing process. By comparison, magnetic detection has much larger signals (and better signal-to-noise ratio (SNR)) and can be performed without magnetic particles labeling the bases being in direct contact with the sensor elements, thereby allowing sensor elements to be coated in a protective layer that would prevent interactions with the sequencing chemistries.

For the various embodiments of the disclosure discussed here, a MR sensor device as disclosed has at least the advantage that it takes advantage of similar operating methodology of a magnetic recording read head. It can be used in a simple binary detection process to detect the presence of an introduced DNA base, or it can be used with multiple base reads at the same time (speeding up sequencing). It can also provide flexibility in the choice of MNPs used as tags for the DNA, as both superparamagnetic and ferromagnetic particles are suitable.

One limitation of magnetic detection may be the signal to noise ratio of the magnetic sensors 105. At least one advantage of various embodiments of the disclosure is that the magnetic field-based embodiments use an applied magnetic field, which, generally speaking, reduces magnetic noise in the system. On the other hand, the noise-based detection embodiments take advantage of magnetic noise by using it to detect the presence or absence of magnetic particles (i.e., as a read mechanism). Another advantage is that, because some embodiments detect a single voltage (or resistance) for each sensor element, such a method is very fast and allows for high data collection throughput, which is highly desirable in a sequencing system.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. A sensing device, comprising:
   at least one fluidic channel configured to receive a plurality of molecules to be detected, wherein at least some of the plurality of molecules to be detected are coupled to respective magnetic nanoparticles (MNPs);
   a plurality of magnetoresistive (MR) sensors;
   an insulating material encapsulating the plurality of MR sensors and for providing a barrier between the plurality of MR sensors and contents of the at least one fluidic channel; and
   detection circuitry coupled to each of the plurality of MR sensors,
   wherein:
   a surface of the insulating material within the fluidic channel provides a plurality of sites for binding the plurality of molecules to be detected, the plurality of sites being located among the plurality of MR sensors, and
   the detection circuitry is configured to detect a characteristic of a magnetic noise of each of the plurality of MR sensors, wherein the characteristic of the magnetic noise is influenced by a presence or absence of one or more MNPs at each of the plurality of sites.

2. The sensing device of claim 1, wherein the characteristic is an amplitude of the magnetic noise at a particular frequency or within a particular frequency band.

3. The sensing device of claim 2, wherein the detection circuitry comprises:
   a bias element coupled to at least one of the plurality of MR sensors and configured to generate a bias across the at least one of the plurality of MR sensors;

a first low pass filter and amplifier combination coupled to the at least one of the plurality of MR sensors to filter and amplify a signal from the at least one of the plurality of MR sensors;

a reference oscillator configured to generate a reference signal having a particular frequency chosen to maximize a change in the signal at the particular frequency when at least one of the one or more MNPs labeling a particular molecule type is detected by the at least one of the plurality of MR sensors at one or more of the plurality of sites;

a mixer coupled to the reference oscillator and an output of the first low pass filter and amplifier combination, wherein the mixer is configured to mix an output signal from the first low pass filter and amplifier combination with the reference signal;

a second low pass filter and amplifier combination coupled to the mixer; and an envelope detector configured to receive an output signal from the second low pass filter and amplifier combination and provide a signal for detection, wherein a voltage of the signal for detection is proportional to the amplitude of the magnetic noise.

4. The sensing device of claim 1, wherein the characteristic is a fluctuation of the magnetic noise.

5. The sensing device of claim 4, wherein the detection circuitry comprises:

a bias element coupled to at least one of the plurality of MR sensors and configured to generate a bias across the at least one of the plurality of MR sensors;

an amplifier coupled to the at least one of the plurality of MR sensors to filter and amplify a signal from the at least one of the plurality of MR sensors;

a filter coupled to the amplifier; and an envelope detector configured to receive an output signal from the filter and provide a signal for detection, wherein a voltage of the signal for detection is proportional to the fluctuation of the magnetic noise.

6. The sensing device of claim 1, wherein the characteristic is a phase of the magnetic noise.

7. The sensing device of claim 6, wherein the detection circuitry comprises a phase locked loop configured to provide an error signal output that corresponds to the phase of the magnetic noise.

8. The sensing device of claim 1, further comprising:

a plurality of lines coupled to the plurality of MR sensors; and a plurality of selector elements, each of the plurality of selector elements coupled to at least one of the plurality of lines and to a respective one of the plurality of MR sensors.

9. The sensing device of claim 8, wherein the plurality of selector elements comprises a transistor.

10. The sensing device of claim 8, wherein the plurality of selector elements comprises an in-stack selector element.

11. The sensing device of claim 1, wherein the sensing device is a sequencing device, and wherein the molecules are biologic molecules.

12. The sensing device of claim 11, wherein the biologic molecules are nucleic acid molecules.

13. The sensing device of claim 1, wherein at least one of the MR sensors comprises a pinned layer, a free layer, and a spacer layer disposed between the pinned layer and the free layer, and wherein, absent an applied magnetic field and absent the presence of one or more MNPs, an orientation of a magnetic moment of the free layer is approximately 90° from an orientation of a magnetic moment of the pinned layer.

14. The sensing device of claim 1, wherein:

a first subset of the plurality of MR sensors is arranged in a first row;

a second subset of the plurality of MR sensors is arranged in a second row, the second row being parallel to the first row; and the at least one fluidic channel is disposed between the first and second rows.

15. The sensing device of claim 1, further comprising a selector element.

16. The sensing device of claim 15, wherein the selector element comprises a transistor.

17. The sensing device of claim 15, wherein the selector element is an in-stack selector element.

18. The sensing device of claim 1, further comprising a magnetic component configured to apply a magnetic field across the sensing device.

19. The sensing device of claim 18, wherein the magnetic component comprises one or more of an electromagnet, a distributed coil, a solenoid, a permanent magnet, or a super-conducting magnet.

20. A method of using the sensing device of claim 1, comprising:

applying a magnetic field across the sensing device; and the detection circuitry detecting the characteristic of the magnetic noise of each of the plurality of MR sensors.

21. The method of claim 20, wherein, in a vicinity of each of the plurality of MR sensors, the applied magnetic field is (a) in a substantially same direction as a field emanating from the one or more MNPs, or (b) in a substantially opposite direction from the field emanating from the one or more MNPs.

22. A method of fabricating the sensing device of claim 1, wherein at least one of the MR sensors comprises a pinned layer, a free layer, and a spacer layer disposed between the pinned layer and the free layer, and wherein an orientation of a magnetic moment of the free layer is approximately 90° from an orientation of a magnetic moment of the pinned layer, and wherein the method comprises at least one of:

applying a hard bias field;

patterning the at least one of the MR sensors into a rectangle or ellipse;

etching the free and pinned layers along an axis to induce texturing; or using perpendicular magnetic anisotropy to pull the free layer out of plane while keeping the pinned layer in the plane of the at least one of the MR sensors.

23. A sensing device, comprising:

at least one fluidic channel configured to receive a plurality of molecules to be detected, wherein at least some of the plurality of molecules to be detected are coupled to respective magnetic nanoparticles (MNPs);

a plurality of magnetoresistive (MR) sensors;

an insulating material encapsulating the plurality of MR sensors and for providing a barrier between the plurality of MR sensors and a contents of the at least one fluidic channel; and detection circuitry coupled to each of the plurality of MR sensors, wherein:

a surface of the insulating material within the fluidic channel provides a plurality of sites for binding the plurality of molecules to be detected, the plurality of sites being located among the plurality of MR sensors, and the detection circuitry is configured to detect one or more of a change in resistance, current, or voltage drop across each of the plurality of MR sensors, wherein the change in resistance, current, or voltage drop is influenced by the presence or absence of one or more MNPs at each of the plurality of sites.

24. The sensing device of claim 23, wherein the detection circuitry is further configured to report the change in resistance, current, or voltage drop as a binary output that indicates the presence or absence of a particular MNP labeling a particular molecule type at each of the plurality of sites.

25. The sensing device of claim 23, wherein the detection circuitry is further configured to report the change in resistance, current, or voltage drop at each of the plurality of sites as a quantized output having one of a plurality of levels, at least some of the levels being used to differentiate MNPs having different saturation magnetizations, with each saturation magnetization corresponding to a particular MNP labeling a particular molecule type.

26. The sensing device of claim 23, further comprising:
a plurality of lines coupled to the plurality of MR sensors; and
a plurality of selector elements, each of the plurality of selector elements coupled to at least one of the plurality of lines and to a respective one of the plurality of MR sensors.

27. The sensing device of claim 26, wherein the plurality of selector elements includes a transistor.

28. The sensing device of claim 26, wherein the plurality of selector elements comprises an in-stack selector element.

29. The sensing device of claim 23, wherein the sensing device is a sequencing device, and wherein the molecules are biologic molecules.

30. The sensing device of claim 29, wherein the biologic molecules are nucleic acid molecules.

31. The sensing device of claim 23, wherein each of the MR sensors comprises a pinned layer, a free layer, and a spacer layer disposed between the pinned layer and the free layer, and wherein, absent an applied magnetic field and absent the presence of one or more MNPs, an orientation of a magnetic moment of the free layer is approximately 90° from an orientation of a magnetic moment of the pinned layer.

32. The sensing device of claim 23, wherein:
a first subset of the plurality of MR sensors is arranged in a first row;
a second subset of the plurality of MR sensors is arranged in a second row, the second row being parallel to the first row; and
the at least one fluidic channel is disposed between the first and second rows.

33. The sensing device of claim 23, further comprising a selector element.

34. The sensing device of claim 33, wherein the selector element comprises a transistor.

35. The sensing device of claim 33, wherein the selector element is an in-stack selector element.

36. A method of fabricating the sensing device of claim 23, wherein at least one of the MR sensors comprises a pinned layer, a free layer, and a spacer layer disposed between the pinned layer and the free layer, and wherein an orientation of a magnetic moment of the free layer is approximately 90° from an orientation of a magnetic moment of the pinned layer, and wherein the method comprises at least one of:
applying a hard bias field;
patterning the at least one of the MR sensors into a rectangle or ellipse;
etching the free and pinned layers along an axis to induce texturing; or
using perpendicular magnetic anisotropy to pull the free layer out of plane while keeping the pinned layer in the plane of the at least one of the MR sensors.

\* \* \* \* \*